US010640546B2

(12) United States Patent
Tirrell et al.

(10) Patent No.: US 10,640,546 B2
(45) Date of Patent: May 5, 2020

(54) NON-CANONICAL INSULINS AND THEIR USES

(71) Applicant: California Institute of Technology, Pasadena, CA (US)

(72) Inventors: David A. Tirrell, Pasadena, CA (US); Seth Lieblich, Pasadena, CA (US); Katharine Y. Fang, Pasadena, CA (US); Howard C. Zisser, Santa Barbara, CA (US)

(73) Assignee: California Institute of Technology, Pasadena, CA (US)

( * ) Notice: Subject to any disclaimer, the term of this patent is extended or adjusted under 35 U.S.C. 154(b) by 197 days.

(21) Appl. No.: 14/735,742

(22) Filed: Jun. 10, 2015

(65) Prior Publication Data

US 2015/0353619 A1 Dec. 10, 2015

Related U.S. Application Data

(60) Provisional application No. 62/010,271, filed on Jun. 10, 2014.

(51) Int. Cl.
*C07K 14/62* (2006.01)

(52) U.S. Cl.
CPC .......... *C07K 14/62* (2013.01); *C07K 2319/21* (2013.01)

(58) Field of Classification Search
CPC .................................................... C07K 14/62
See application file for complete search history.

(56) References Cited

U.S. PATENT DOCUMENTS

| | | | | |
|---|---|---|---|---|
| 5,514,646 A * | 5/1996 | Chance | ........... | C07K 14/62 435/68.1 |
| 5,700,662 A | 12/1997 | Chance et al. | | |
| 8,962,794 B2 * | 2/2015 | Madsen | ........... | C07K 14/62 530/303 |
| 2010/0144592 A1* | 6/2010 | Bjerregaard | ........... | A61K 9/08 514/10.3 |
| 2011/0098440 A1* | 4/2011 | Madsen | ........... | C07K 14/62 530/303 |
| 2013/0022592 A1* | 1/2013 | Vaughn | ........... | A61K 38/28 424/94.62 |

FOREIGN PATENT DOCUMENTS

| | | | |
|---|---|---|---|
| AU | 4922690 A | * | 8/1990 |
| JP | H02264798 A | | 10/1990 |
| JP | 2010529956 A | | 9/2010 |
| JP | 2010535849 A | | 11/2010 |
| JP | 2010535851 A | | 11/2010 |

OTHER PUBLICATIONS

Tam, et al., Protein Prosthesis: 1,5-Disubstituted [1,2,3]triazoles as cis-Peptide Bond Surrogates, JACS Communications, Web Published Oct. 3, 2007.*
Havelund, et al., The Mechanism of Protraction of Insulin Detemir, a Long-acting, Acylated Analog of Human Insulin, Pharmaceutical Research, vol. 21, No. 8, Aug. 2004.*
PubChem CID 440015, National Center for Biotechnology Information. PubChem Compound Database; CID=440015.*
Chorghadea, Practical syntheses of 4-fluoroprolines, J Fluor Chem. Sep. 2008; 129(9): 781-784 (Year: 2008).*
PubChem CID: 10057550 (Year: 2006).*
Owens, Insulin aspart: a review, Expert Opin. Drug Metab. Toxicol. 2006, 2:793-804 (Year: 2006).*
Owens (Insulin aspart: a review, Expert Opin. Drug Metab. Toxicol. 2006, 2:793-804, of record) (Year: 2006).*
Chorghade (Practical syntheses of 4-fluoroprolines, J Fluor Chem. Sep. 2008; 129(9): 781-784, of record) (Year: 2008).*
Havelund (The Mechanism of Protraction of Insulin Detemir, a Long-acting, Acylated Analog of Human Insulin, Pharmaceutical Research, vol. 21, No. 8, Aug. 2004, of record) (Year: 2004).*
Brange (Toward Understanding Insulin Fibrillation, Journal of Pharmaceutical Sciences 1997, 86:517-525, of record) (Year: 1997).*
Pandey (Proline Editing: A General and Practical Approach to the Synthesis of Functionally and Structurally Diverse Peptides. Analysis of Steric versus Stereoelectronic Effects of 4-Substituted Prolines on Conformation within Peptides, JACS 2013, 135:4333-4363) (Year: 2013).*
Zawadzki (Clinical Review of Application NDA 20-986, dated Mar. 12, 2008 and available online Jul. 19, 2009 as confirmed using Web Achieve downloaded Mar. 27, 2018 from the following website: http://www.fda.gov/downloads/Drugs/DevelopmentApprovalProcess/DevelopmentResources/ucm072453.pdf, of record) (Year: 2009).*
International Search Report for PCT/US2015/035096 completed dated Sep. 6, 2015.
Brange et al., "Toward Understanding Insulin Fibrillation," J Pharm Sci, 86(5): 517-525 (1997).
Extended European Search Report issued by the European Patent Office in corresponding Application No. EP 15 80 7207, dated Dec. 22, 2017.
Borgogno et al., "The Impact of Either 4-R-Hydroxyproline or 4-R-Floroproline on the conformation and $SH3_{m\_cort}$ Binding of HPK1 Proline-Rich Peptide," Amino Acids, 44(2): 607-614 (2013).
Brange et al., "Monomeric Insulins Obtained by Protein Engineering and their Medical Implications," Nature, 333: 679-682 (1988).
Crespo et al., "Rational Design of Protein Stability: Effect of (2S,4R)-4-Floroproline on the Stability and folding Pathway of Ubiquitin," Plos One, 6(5): e19425 (2011).
Holmgren et al., "A Hyperstable Collagen Mimic," Chemistry & Biology, 6(2): 63-70 (1999).
Salwiczek et al., "Fluorinated Amino Acids: Compatibility with Native Protein Structures and Effects on Protein-Protein Interactions," Chemical Social Review, 41(6): 2135-2171 (2012).

(Continued)

Primary Examiner — Lianko G Garyu

(74) Attorney, Agent, or Firm — Foley Hoag LLP; David P. Halstead; Alexander J. Chatterley

(57) ABSTRACT

In some aspects, the invention relates to an insulin derivative, comprising a cyclic amino acid at position B28 or B29, wherein the cyclic amino acid is not L-proline. In some aspects, the invention relates to a method of making said insulin derivative. In some aspects, the invention relates to a pharmaceutical composition comprising said insulin derivative. In some aspects the invention relates to a method of treating a disease or condition in a subject comprising administering to the subject a composition comprising said insulin derivative.

20 Claims, 15 Drawing Sheets

Specification includes a Sequence Listing.

(56) References Cited

OTHER PUBLICATIONS

Steiner et al., "Synthetic Biology of Proteins: Tuning GFPs Folding and Stability with Fluoroproline," PLoS One, 3(2): e1680 (2008).
Newberry et al., "4-Fuoroprolines: Conformational Analysis and Effects on the Stability and Folding of Peptides and Proteins," Top Heterocycl Chem, 48:1-25 (2017).
Torbeev et al., "Both the Cis-Trans Equilibrium and Isomerization Dynamics of a single Proline Amide Modulate b2-Mocroglobulin Amyloid Assembly," PNAS, 110(50):20051-20056 (2013).

* cited by examiner

Figure 1

```
Insulin A Chain        S─────────────S              (SEQ ID NO:1)
                       │             │
A1  A2  A3  A4  A5  A6  A7  A8  A9  A10 A11 A12 A13 A14 A15 A16
Gly-Ile-Val-Glu-Gln-Cys-Cys-Thr-Ser-Ile-Cys-Ser-Leu-Tyr-Gln-Leu-
                                    │
                                    S
                                    │
Insulin B Chain        S                            (SEQ ID NO:2)
                       │
Phe-Val-Asn-Gln-His-Leu-Cys-Gly-Ser-His-Leu-Val-Glu-Ala-Leu-Tyr-
B1  B2  B3  B4  B5  B6  B7  B8  B9  B10 B11 B12 B13 B14 B15 B16

A17 A18 A19 A20 A21
        Glu-Asn-Tyr-Cys-Asn
                     │
                     S
                     │
                     S
                     │
            Leu-Val-Cys-Gly-Glu-Arg-Gly-Phe-Phe-Tyr-Thr-Xaa-Xaa-Thr
            B17 B18 B19 B20 B21 B22 B23 B24 B25 B26 B27 B28 B29 B30
```

IBs: Inclusion Bodies
AS: After sulfitolysis
Mis: misfolded proteins

NON-CANONICAL INSULINS AND THEIR USES

PRIORITY CLAIM

This application claims priority to U.S. Provisional Patent Application No. 62/010,271, filed on Jun. 10, 2014, which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Aug. 6, 2015, is named CTH-018.01_SL.txt and is 17,912 bytes in size.

BACKGROUND

The World Health Organization projects diabetes to be the 7th leading cause of death in 2030, with one in every ten adults (more than 500 million people) expected to have the condition. Current diabetic therapies have a market of at least $35 billion (US) and the value is predicted to rise steeply due to changes in lifestyle and increasing prevalence of diabetes. The size and rapid growth of this market make it one of the largest sectors in global healthcare.

Recombinant human insulin is the mainstay of the diabetes drug market. Standard pharmaceutical preparations of recombinant human insulin contain zinc ions along with a phenolic preservative. The addition of zinc ions stabilizes the protein formulation by inducing the formation of an insulin hexamer. However, a delay in activity is observed despite the soluble state of insulin in these formulations. This delay has been associated with the time required for the hexamer to dissociate into the active monomeric state before it is absorbed from the interstitium. Thus, decreasing the propensity of insulin to self-associate while maintaining long-term stability could minimize the lag time before onset of activity following insulin administration.

Significant research investment has been dedicated to engineering insulin analogs with improved therapeutic properties, including longer duration of action, increased efficacy and increased speed of action. Extensive biophysical characterization of the aggregation of native insulin has made it possible to engineer insulin analogs with improved therapeutic profiles. These include rapid-acting insulin lispro (Humalog®, Eli Lilly), in which the positions of Lys29 and Pro28 in the insulin B-chain are switched, and insulin aspart (Novalog®, Novo Nordisk), in which Pro28 is replaced by aspartate. Additionally, insulin glulisine (Apidra®, Sanofi-Aventis) comprises a substitution of Asn3 in the insulin B-chain with Lysine and a substitution of Lys29 in the B-chain with glutamate. Nevertheless, additional engineering of insulin analogs may further improve its therapeutic profile.

SUMMARY

In some aspects, the invention relates to an insulin derivative, comprising a cyclic amino acid at position B28 or B29, wherein the cyclic amino acid is not L-proline.

In some aspects, the invention relates to a method of making an insulin derivative, comprising incubating cells comprising an insulin gene in a medium comprising a cyclic amino acid, wherein the cyclic amino acid is not L-proline.

In some aspects, the invention relates to a pharmaceutical composition, comprising an insulin derivative comprising a cyclic amino acid at position B28 or B29, wherein the cyclic amino acid is not L-proline.

In some aspects the invention relates to a method of treating a disease or condition in a subject, comprising administering to the subject a composition comprising an insulin derivative comprising a cyclic amino acid at position B28 or B29, wherein the cyclic amino acid is not L-proline. The disease or condition may be, for example, hyperglycemia, type 2 diabetes, impaired glucose tolerance, type 1 diabetes, obesity, metabolic syndrome X, or dyslipidemia.

DESCRIPTION OF THE FIGURES

FIG. 1 depicts the sequence and disulfide bonding pattern of various insulin derivatives according to some embodiments of the invention. The amino acid sequences correspond to the human insulin A chain (SEQ ID NO:1) and the human insulin B chain comprising substitutions in the B28 and B29 positions (SEQ ID NO:2). In various embodiments, the substitutions at the B28 and B29 positions may comprise the replacement of the Pro28 and/or Lys29 of human insulin with a cyclic amino acid, wherein the cyclic amino acid is not proline.

Figure 7:
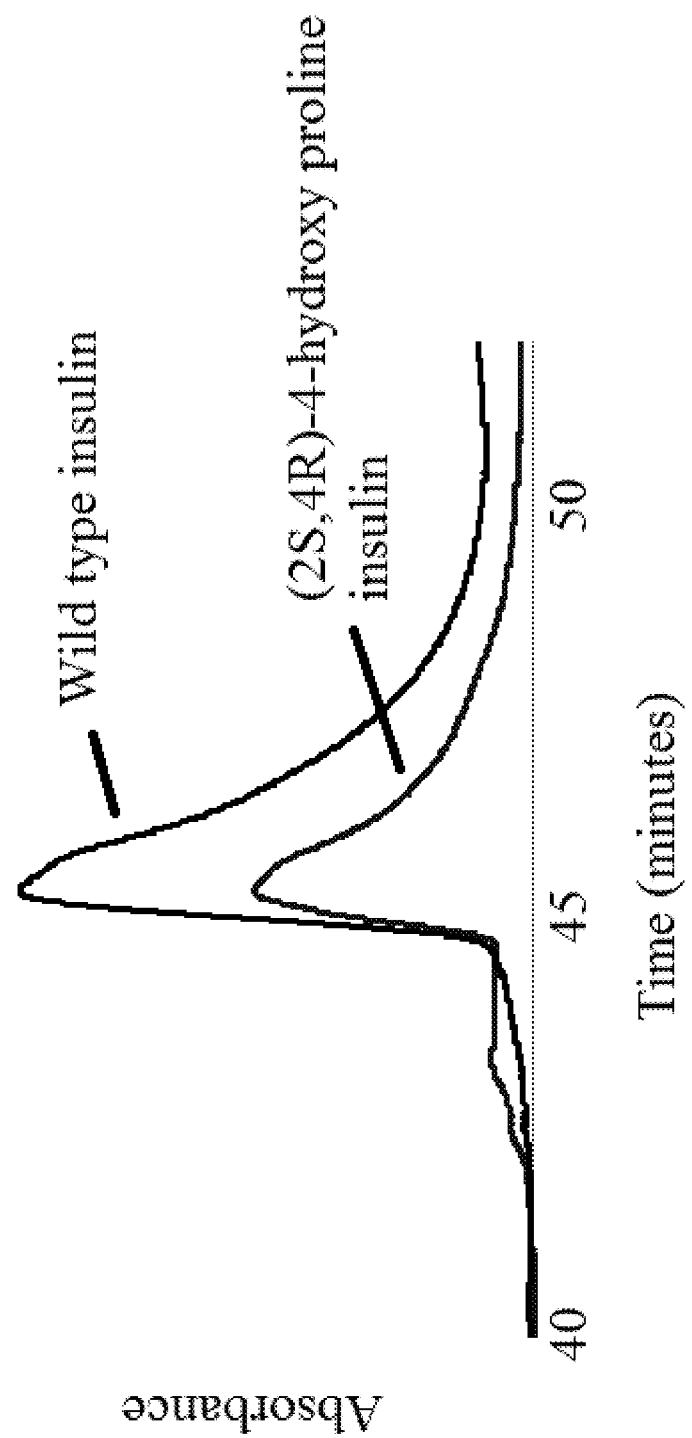

FIG. 7 shows an HPLC trace of mature, wild type insulin and mature insulin comprising a substitution of (2S,4R)-4-hydroxy proline at the insulin B chain B28 position.

Figure 8:
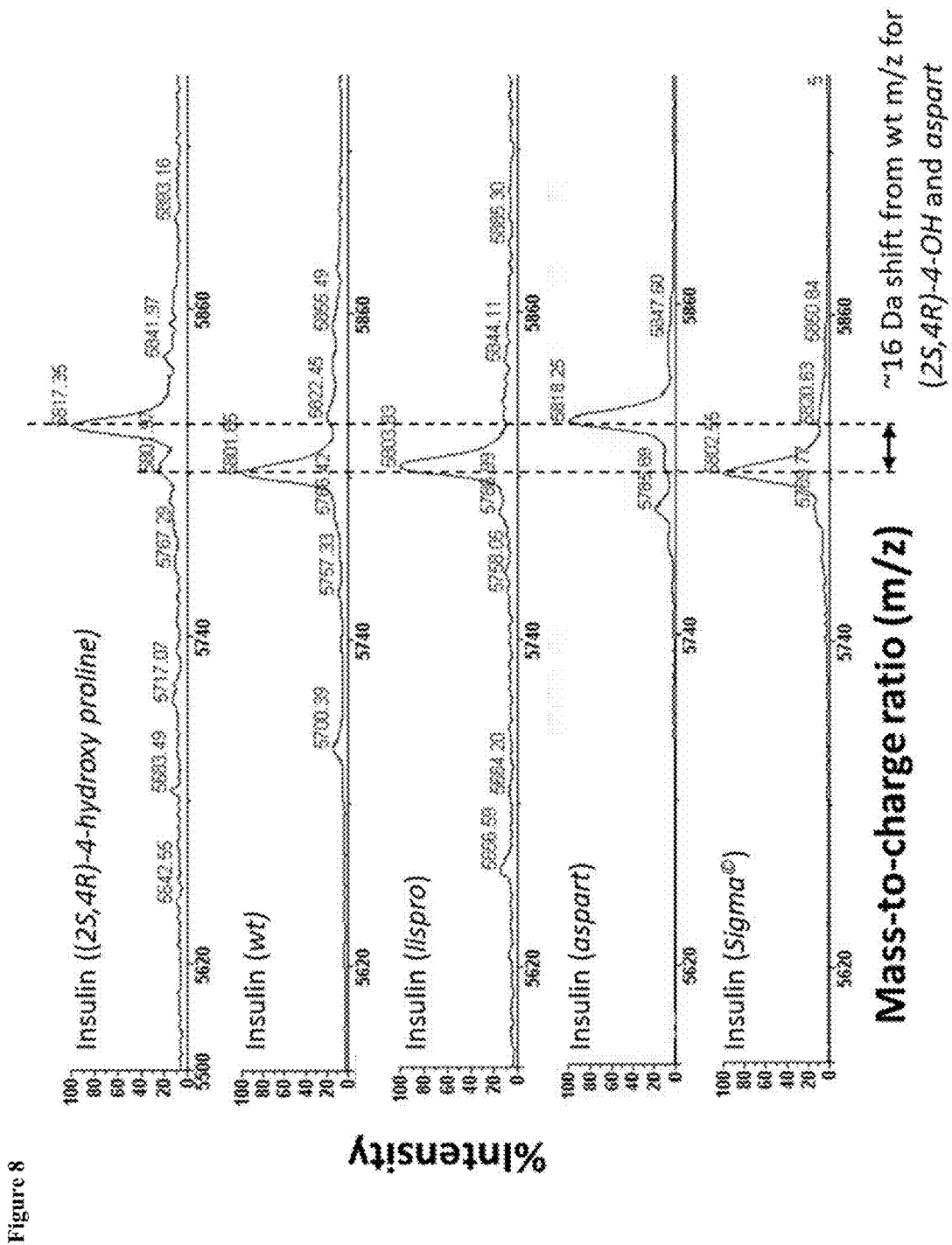

FIG. 8 shows MALDI-MS spectra for mature insulins, including (2S, 4R)-4-hydroxy-L-proline insulin and wild type insulin, which were produced according to the methods described herein, and insulin lispro, insulin aspart, and commercially available wild type insulin. The apparent molecular weights for the insulin fragments vary from those shown in FIG. 6 due to the calibration of the MALDI-MS instrument and because the insulins are mature insulins. Notably, the molecular weight of the peptide corresponding to the mature, wild type insulin produced according to the methods described herein is equivalent to the molecular weights of commercial insulin and insulin lispro, which reverses the order of proline and lysine at insulin B chain positions B28 and B29, and thus, does not affect the protein's molecular weight. The (2S, 4R)-4-hydroxy-L-proline insulin derivative displayed an expected 16 Dalton shift in molecular weight. Similarly, insulin aspart, which comprises a substitution of proline (MW=115) with aspartate (MW=132), displayed an expected 17 Dalton shift in molecular weight.

Figure 9:
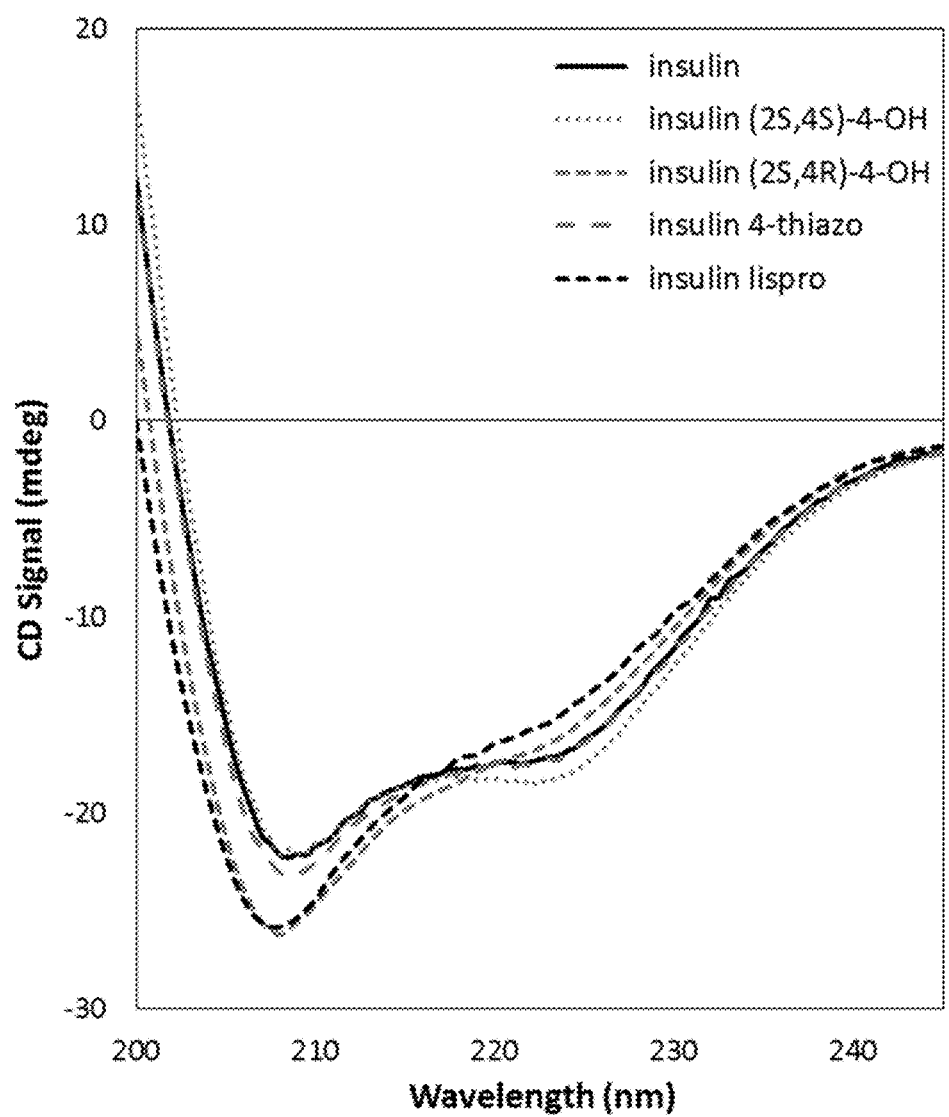

FIG. 9 shows circular dichroism ("CD") spectra for insulin derivatives comprising (2S, 4S)-4-hydroxy-L-proline ("insulin (2S,4S)-4-OH"), (2S, 4R)-4-hydroxy-L-proline ("insulin (2S,4R)-4-OH"), and (4R)-1,3-thiazolidine-4-carboxylic acid ("insulin 4-thiazo") at the insulin B chain B28 position, as well as CD spectra for wild type insulin ("insulin") and insulin lispro.

Figure 10:
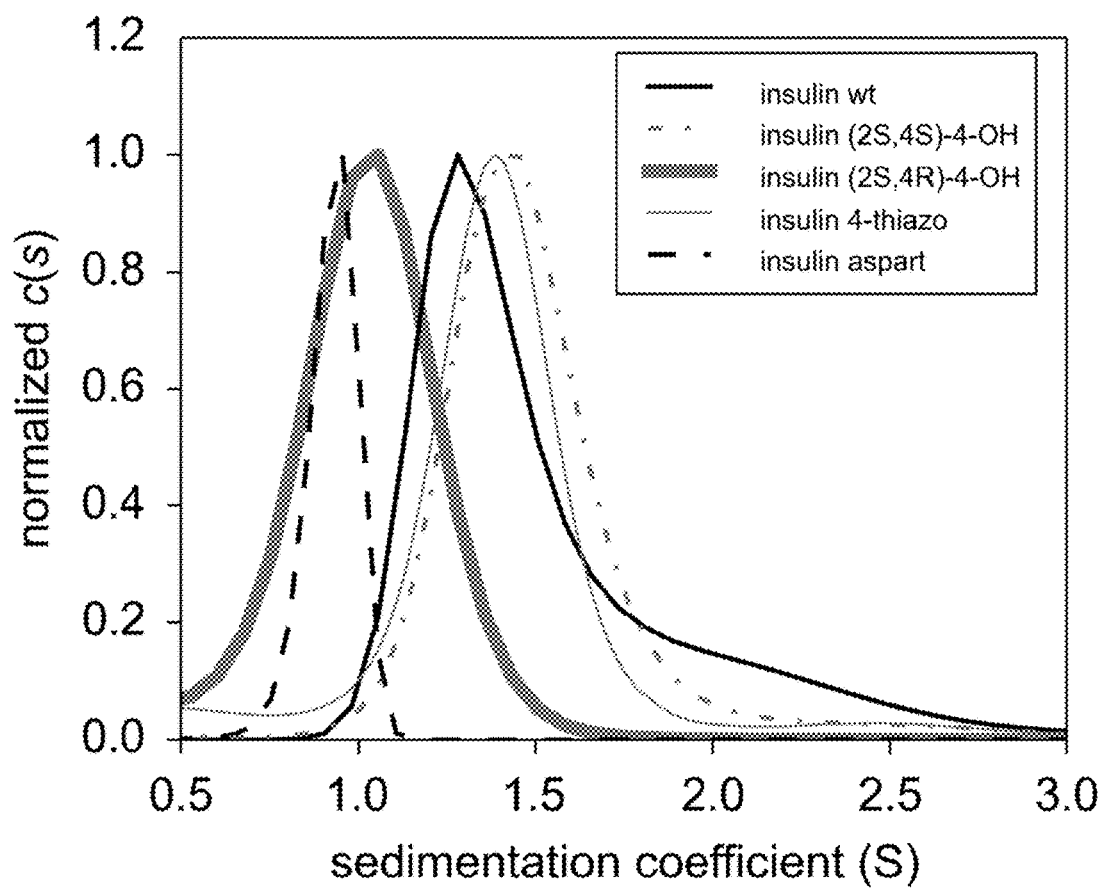

FIG. 10 shows analytical ultracentrifugation results for insulin derivatives comprising (2S, 4S)-4-hydroxy-L-proline ("insulin (2S,4S)-4-OH"), (2S, 4R)-4-hydroxy-L-proline ("insulin (2S,4R)-4-OH"), or (4R)-1,3-thiazolidine-4-carboxylic acid ("insulin 4-thiazo") at the insulin B chain B28 position as well as wild type insulin and insulin aspart.

Figure 11:
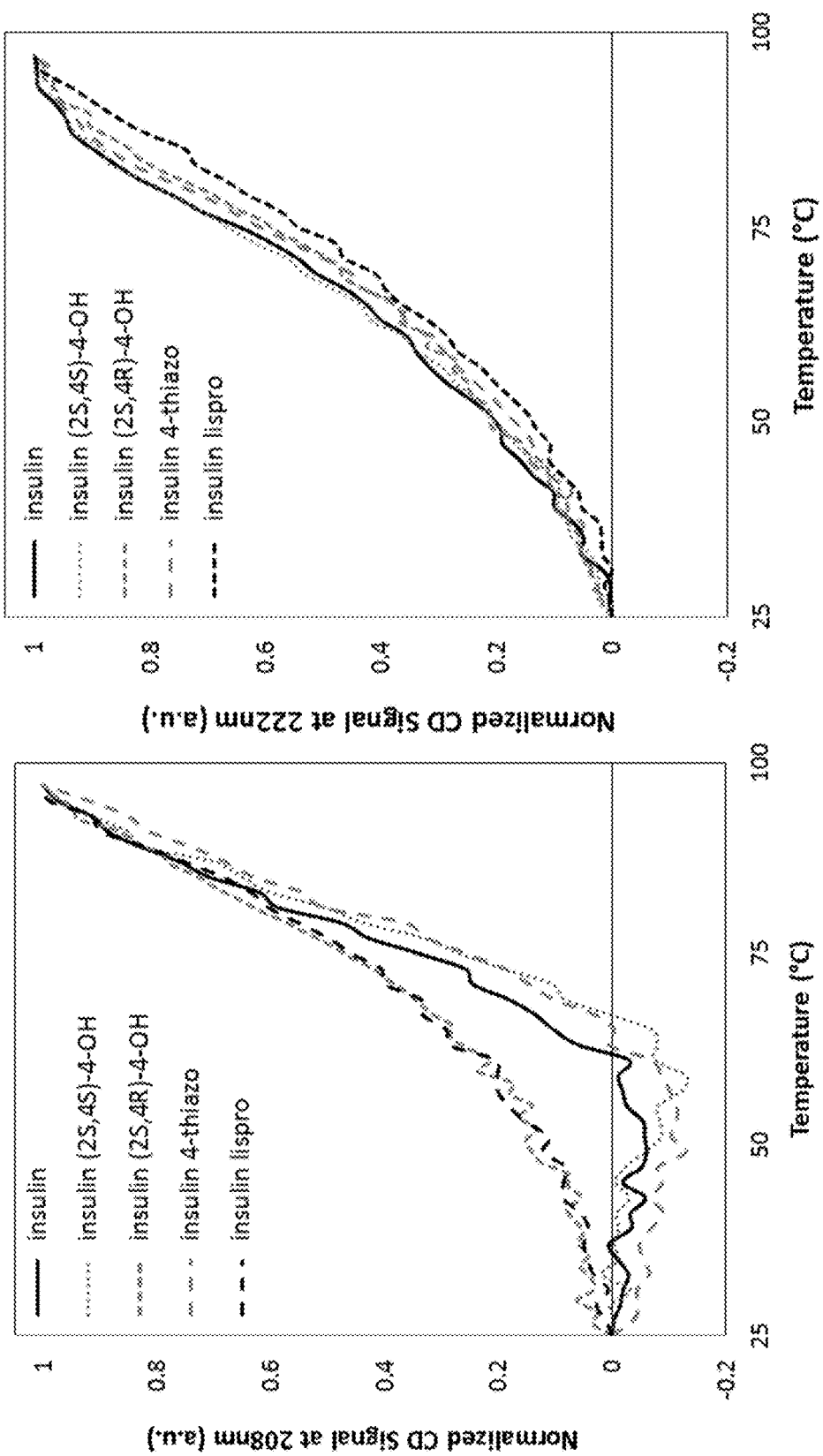

FIG. 11 shows melting curves for insulin derivatives comprising (2S, 4S)-4-hydroxy-L-proline ("insulin (2S,4S)-4-OH"), (2S, 4R)-4-hydroxy-L-proline ("insulin (2S,4R)-4-OH"), or (4R)-1,3-thiazolidine-4-carboxylic acid ("insulin 4-thiazo") at the insulin B chain B28 position as well as wild type insulin and insulin lispro. The melting curves track changes in ellipticity during heating from 25° C. to 95° C.

Figure 12:
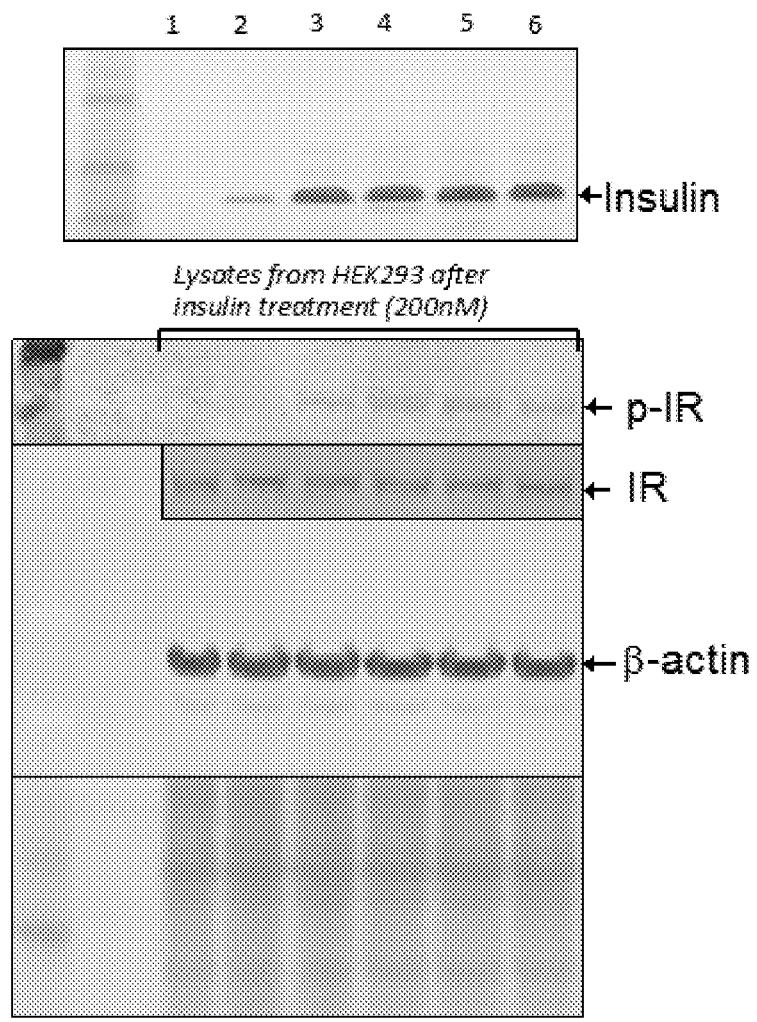

FIG. 12 depicts western blots of HEK293 whole cell lysates that were treated with PBS vehicle (lane 1), 20 nM wild type insulin (lane 2), 200 nM of an insulin derivative comprising (2S, 4S)-4-hydroxy-L-proline at the B28 position (lane 3), 200 nM of an insulin derivative comprising (2S, 4R)-4-hydroxy-L-proline at the B28 position (lane 4), 200 nM of an insulin derivative comprising (4R)-1,3-thiazolidine-4-carboxylic acid at the B28 position (lane 5), and 200 nM of wild type insulin (lane 6). The band labeled "Insulin" is an insulin band from an SDS-PAGE gel of the insulin preparations that were added to the HEK293 cells. The band labeled "p-IR" corresponds to a western blot for phosphorylated insulin receptor. The band labeled "IR" corresponds to a western blot for total insulin receptor. The band labeled "β-actin" corresponds to a western blot for β-actin, which was used as a loading control. The bottom panel depicts total protein run on the gel.

Figure 13:
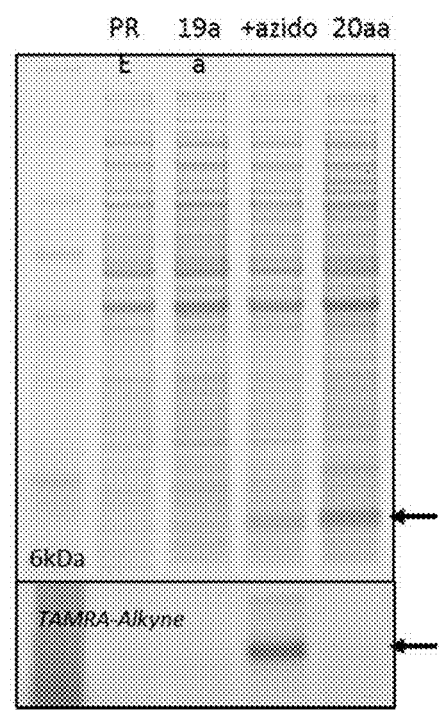

FIG. 13 shows a polyacrylamide gel that was visualized for TAMRA fluorophore (bottom panel) and by InstaBlue stain (top panel). The lane labeled "PR" corresponds to a cell lysate that was clicked to TAMRA alkyne for cells incubated in media comprising L-proline. The lane labeled "+azido" corresponds to a cell lysate that was clicked to TAMRA alkyne for cells incubated in media comprising (2S,4S)-4-azido-L-proline. The "+azido" lane displays protein that was visible by imaging for the TAMRA fluorophore, corresponding to the molecular weight for the proinsulin construct; this band was not visible by imaging for the TAMRA fluorophore in control lanes.

DETAILED DESCRIPTION

Definitions

The articles "a" and "an" are used herein to refer to one or to more than one (i.e., to at least one) of the grammatical object of the article. By way of example, "an element" means one element or more than one element.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CF$_3$, —CN and the like. Exemplary substituted alkyls are described below. Cycloalkyls can be further substituted with alkyls, alkenyls, alkoxys, alkylthios, aminoalkyls, carbonyl-substituted alkyls, —CF$_3$, —CN, and the like.

The term "alkylamino", as used herein, refers to an amino group substituted with at least one alkyl group.

The term "alkylthio", as used herein, refers to a thiol group substituted with an alkyl group and may be represented by the general formula alkylS—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The terms "amide nitrogen" and "amine nitrogen" as used herein, refer to the nitrogen of an amino acid that forms a peptide bond with a carboxyl group in a protein. For a amino acids, the amide nitrogen (or amine nitrogen) forms a covalent bond with the a carbon of the amino acid. In the context of the protein, amide nitrogens typically form a covalent bond with the carboxyl group of an adjacent amino acid. An amide nitrogen (or amine nitrogen) may also form a covalent bond with an additional atom, e.g., in cyclic amino acids, such as proline.

The term "aminoalkyl", as used herein, refers to an alkyl group substituted with an amino group.

The term "aralkyl", as used herein, refers to an alkyl group substituted with an aryl group. The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond. "Carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be susbstituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The term "carbamate" is art-recognized and refers to a group

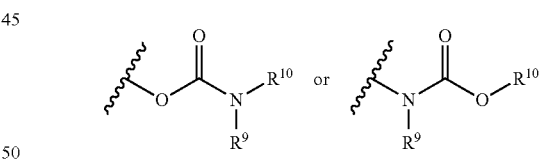

wherein R$^9$ and R$^{10}$ independently represent hydrogen or a hydrocarbyl group, such as an alkyl group, or R$^9$ and R$^{10}$ taken together with the intervening atom(s) complete a heterocycle having from 4 to 8 atoms in the ring structure.

The term "carbocyclylalkyl", as used herein, refers to an alkyl group substituted with a carbocycle group.

The term "carbonate" is art-recognized and refers to a group —OCO$_2$—R$^{10}$, wherein R$^{10}$ represents a hydrocarbyl group.

The term "carboxy", as used herein, refers to a group represented by the formula —CO$_2$H.

Throughout this specification and claims, the word "comprise" or variations such as "comprises" or "comprising" will be understood to imply the inclusion of a stated integer or groups of integers but not the exclusion of any other integer or group of integers.

The term "cyclic amino acid" as used herein, refers to any amino acid comprising either (a) a heterocycle that comprises the amine nitrogen or amide nitrogen or (b) a carbocycle comprising a backbone carbon, e.g., an α carbon. For example, for a amino acids, the term "cyclic amino acid" may refer to an amino acid comprising a heterocycle that comprises the amine nitrogen (or amide nitrogen, e.g., for amino acids incorporated into an insulin derivative), the α carbon, and a β carbon. For example, proline is a cyclic amino acid comprising a heterocycle comprising an amine nitrogen, α carbon, β carbon, γ carbon, and δ carbon. Unless otherwise apparent by context, the term "cyclic amino acid" as used herein refers to a cyclic amino acid other than L-proline.

The term "diabetes" as used herein, refers to diabetes mellitus, such as type 1 diabetes mellitus, type 2 diabetes mellitus, or gestational diabetes.

As used herein, the terms "effective amount" and "therapeutically effective amount" mean a dosage sufficient to produce a desired result, e.g., to decrease blood glucose levels.

The term "ester", as used herein, refers to a group —C(O)OR$^{10}$ wherein R$^{10}$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The term "heteroalkyl", as used herein, refers to a saturated or unsaturated chain of carbon atoms and at least one heteroatom, wherein no two heteroatoms are adjacent. The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like. Heterocyclyl groups can also be substituted by oxo groups. For example, "heterocyclyl" encompasses both pyrrolidine and pyrrolidinone.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to, aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

As used herein, the term "oxo" refers to a carbonyl group. When an oxo substituent occurs on an otherwise saturated group, such as with an oxo-substituted cycloalkyl group (e.g., 3-oxo-cyclobutyl), the substituted group is still intended to be a saturated group. When a group is referred to as being substituted by an "oxo" group, this can mean that a carbonyl moiety (i.e., —C(=O)—) replaces a methylene unit (i.e., —CH2-).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "prevent" is art-recognized, and when used in relation to a condition, is well understood in the art, and includes administration of a composition which reduces the likelihood of, or delays the onset of, the condition in a subject relative to a subject which does not receive the composition.

The term "silyl" refers to a silicon moiety with three hydrocarbyl moieties attached thereto.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group $OSO_3H$, or a pharmaceutically acceptable salt thereof.

The term "sulfonamide" is art-recognized and refers to the group represented by the general formulae

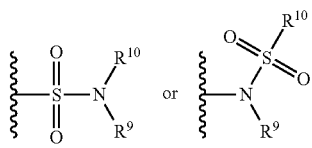

wherein $R^9$ and $R^{10}$ independently represents hydrogen or hydrocarbyl, such as alkyl, or $R^9$ and $R^{10}$ taken together with the intervening atom(s) complete a heterocycle having from 4 to 8 atoms in the ring structure.

The term "sulfoxide" is art-recognized and refers to the group $S(O)—R^{10}$, wherein $R^{10}$ represents a hydrocarbyl.

The term "sulfonate" is art-recognized and refers to the group $SO_3H$, or a pharmaceutically acceptable salt thereof.

The term "sulfone" is art-recognized and refers to the group $S(O)_2—R^{10}$, wherein $R^{10}$ represents a hydrocarbyl.

The term "thioalkyl", as used herein, refers to an alkyl group substituted with a thiol group.

The term "thioester", as used herein, refers to a group —$C(O)SR^{10}$ or $SC(O)R^{10}$ wherein $R^{10}$ represents a hydrocarbyl.

The term "thioether", as used herein, is equivalent to an ether, wherein the oxygen is replaced with a sulfur.

The terms "transforming" and "transfecting" are used interchangeably herein and refer to the introduction of a nucleic acid into a cell, e.g., to produce a recombinant cell. A nucleotide sequence encoded by the nucleic acid may or may not be inheritable to the progeny of the cell. Transfection, for example, may be stable (i.e. the nucleic acid is integrated into the genome of a cell and thereby inheritable to the progeny of the cell) or transient (i.e., wherein the expression of a nucleotide sequence encoded by the nucleic acid is lost after a period of time).

As used herein, the terms "treat", "treating", and "treatment" include inhibiting the condition, e.g., reducing the onset of symptoms of a condition, disorder, or disease, such as diabetes. These terms also encompass therapy. Treatment means any manner in which the symptoms of a condition, disorder, or disease are ameliorated or otherwise beneficially altered. Preferably, the subject in need of such treatment is a mammal, such as a human, pet (e.g., cat or dog), or farm animal.

The term "urea" is art-recognized and may be represented by the general formula

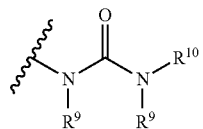

wherein $R^9$ and $R^{10}$ independently represent hydrogen or a hydrocarbyl, such as alkyl, or either occurrence of $R^9$ taken together with $R^{10}$ and the intervening atom(s) complete a heterocycle having from 4 to 8 atoms in the ring structure.

I. Insulin Derivatives

In some aspects, the invention relates to an insulin derivative, comprising a cyclic amino acid at position B28 or B29, wherein the cyclic amino acid is not L-proline. The insulin derivative may comprise an A Chain set forth in SEQ ID NO:1 (GIVEQCCTSICSLYQLENYCN). The insulin derivative may comprise a B Chain set forth in SEQ ID NO:2 (FVNQHLCGSHLVEALYLVCGERGFFYTX$_1$X$_2$T), wherein X$_1$ is position B28 and X$_2$ is position B29 (FIG. 1). In preferred embodiments, the insulin derivative comprises three disulfide bonds as depicted in FIG. 1, i.e., a disulfide bond connecting cysteines at positions A6 and A11, a disulfide bond connecting cysteines at positions A7 and B7, and a disulfide bond connecting cysteines at positions A20 and B19. The insulin may comprise substitutions and/or deletions known in the art. For example, position B1 and/or B30 may be deleted, and position A21 and/or B3 may be substituted with a neutrally-charged amino acid, such as alanine, asparagine, glutamine, glycine, or serine.

In some embodiments, the amino acid at position B28 is proline, lysine, aspartate, or glutamate, or the amino acid at position B29 is proline, lysine, aspartate, or glutamate (see, e.g., proinsulin sequences for SEQ ID NO:29 and SEQ ID NO:31). For example, the amino acid at position B29 may be lysine, and the lysine may be conjugated to substituted or unsubstituted alkyl group or acyl group. The lysine may be conjugated to hexadecanedioic acid, e.g., via a γ-L-glutamyl linker. (see, e.g., U.S. Pat. Nos. 8,710,000 and 7,615,532, hereby incorporated by reference). Similarly, the lysine may be conjugated to myristic acid (see, e.g., U.S. Pat. Nos. 6,869,930 and 5,750,497, hereby incorporated by reference).

In some embodiments, the dimer association constant of the insulin derivative is lower than the dimer association constant of unmodified human insulin. For example, the dimer association constant of the insulin derivative may be less than 0.9 times the dimer association constant of unmodified human insulin, such as less than 0.80 times, 0.70 times, 0.60 times, 0.50 times, 0.40 times, 0.30 times, 0.20 times, 0.10, times, 0.095 times, 0.090 times, 0.085 times, 0.080 times, 0.075 times, 0.070 times, 0.065 times, 0.060 times, 0.055 times, 0.050 times, 0.045 times, 0.040 times, 0.035 times, 0.030 times, 0.025 times, 0.020 times, 0.015 times, 0.010 times, 0.0095 times, 0.0090 times, 0.0085 times, 0.0080 times, 0.0075 times, 0.0070 times, 0.0065 times, 0.0060 times, 0.0055 times, 0.0050 times, 0.0045 times, 0.0040 times, 0.0035 times, 0.0030 times, or even less than 0.0025 times the dimer association constant of unmodified human insulin. The dimer association constant of the insulin derivative may be comparable to the dimer associate constant of unmodified insulin. In some embodiments, the dimer association constant of the insulin derivative is higher than the dimer association constant of unmodified human insulin. The dimer association constant may be measured, for example, by circular dichroism spectroscopy, size-exclusion chromatography, analytical ultracentrifugation, or surface plasmon resonance. In some embodiments, the onset of the insulin derivative is faster than the onset of unmodified human insulin, e.g., in a human patient.

In some embodiments, the insulin derivative has a longer shelf life than unmodified human insulin, i.e., under similar conditions. For example, the insulin derivative may have a shelf life that is at least 1 week longer than unmodified human insulin, such as 2, 3, 4, 5, 6, 7, 8, 9, 10, 11, or even 12 weeks longer than unmodified human insulin. The insulin derivative may have a shelf life that is at least 1 month longer than unmodified human insulin, such as 2, 3, 4, 5, 6, 7, 8, 9, 10, 11, 12, 13, 14, 15, 16, 17, or even 18 months longer than unmodified human insulin. The insulin derivative may have a shelf life that is 1 month to 36 months longer than unmodified human insulin, such as 1 month to 30 months, 1 month to 24 months, 1 month to 18 months, 1 month to 18 months, 1 month to 12 months, 1 month to 9 months, or 1 month to 6 months longer than unmodified human insulin. The shelf life of the insulin derivative may be comparable to the shelf life of unmodified human insulin.

In some embodiments, the insulin derivative is more stable than unmodified human insulin, i.e., under similar conditions. The insulin derivative may have a higher thermostability than unmodified human insulin. The insulin derivative may have a higher melting temperature than unmodified human insulin, e.g., as monitored by circular dichroism spectroscopy. For example, the melting temperature of the insulin derivative may be at least 1° C. higher than the melting temperature of unmodified human insulin, such as at least 2° C. higher, at least 3° C. higher, at least 4° C. higher, at least 5° C. higher, at least 6° C. higher, at least 7° C. higher, at least 8° C. higher, at least 9° C. higher, at least 10° C. higher, at least 11° C. higher, at least 12° C. higher, at least 13° C. higher, at least 14° C. higher, at least 15° C. higher, at least 16° C. higher, at least 17° C. higher, at least 18° C. higher, at least 19° C. higher, or at least 20° C. higher. The melting temperature of the insulin derivative may be 1° C. to 50° C. higher than unmodified human insulin, such as 5° C. higher to 40° C. higher or 1° C. higher to 20° C. higher. The melting temperature of the insulin may be comparable to the melting temperature of unmodified human insulin.

II. Cyclic Amino Acids

The cyclic amino acid may be an α amino acid or a β amino acid. In preferred embodiments, the cyclic amino acid is an α amino acid. In preferred embodiments, the cyclic amino acid comprises a heterocycle comprising the amide nitrogen of the amino acid. The cyclic amino acid may comprise a heterocycle comprising the amide nitrogen, the α carbon, and a β atom of the cyclic amino acid. The cyclic amino acid may be an L amino acid or a D amino acid.

The cyclic amino acid may comprise a 3-membered ring, a 4-membered ring, a 5-membered ring, or a 6-membered ring. In some preferred embodiments, the cyclic amino acid comprises a 5-membered ring. In some preferred embodiments, the cyclic amino acid comprises a 5-membered ring consisting the amide nitrogen, the α carbon, a β atom, a γ atom, and a δ atom of the cyclic amino acid. The β atom, γ atom, and δ atom of a five-membered ring may be selected from the group consisting of carbon, nitrogen, oxygen, sulfur, and selenium. In preferred embodiments, the δ atom of a five-membered ring is a carbon atom. In preferred embodiments, at least one of the β atom and γ atom of a five-membered ring is a carbon atom. In some embodiments, the β atom or γ atom of a five-membered ring is selected from the group consisting of nitrogen, oxygen, sulfur, and selenium.

The cyclic amino acid may comprise a saturated heterocycle or an unsaturated heterocycle.

The cyclic amino acid may have a neutral, positive, or negative charge at physiological pH.

The cyclic amino acid may be halogenated. For example, the cyclic amino acid may be fluorinated.

In some embodiments, the cyclic amino acid is a fluoroproline analog, a hydroxyproline analog, or a proline ring analog. The cyclic amino acid may be selected from 3-hydroxyproline, 4-hydroxyproline, aziridine-2-carboxylic acid, azetidine-2-carboxylic acid, piperidine-2-carboxylic acid, 3-carboxy-morpholine, 3-carboxy-thiamorpholine, 4-oxaproline, pyroglutamic acid, 1,3-oxazolidine-4-carboxylic acid, 1,3-thiazolidine-4-carboxylic acid, 3-thiaproline, 4-thiaproline, 3-selenoproline, 4-selenoproline, 4-ketoproline, 3,4-dehydroproline, 4-aminoproline, 4-fluoroproline, 4,4-difluoroproline, 4-chloroproline, 4,4-dichloroproline, 4-bromoproline, 4,4-dibromoproline, 4-methylproline, 4-ethylproline, 4-cyclohexyl-proline, 3-phenylproline, 4-phenylproline, 3,4-phenylproline, 4-azidoproline, 4-carboxy-proline, α-methylproline, α-ethylproline, α-propylproline, α-allylproline, α-benzylproline, α-(4-fluorobenzyl)-proline, α-(2-chlorobenzyl)-proline, α-(3-chlorobenzyl)-proline, α-(2-bromobenzyl)-proline, α-(4-bromobenzyl)-proline, α-(4-methylbenzyl)-proline, α-(diphenylmethyl)-proline, α-(naphthylmethyl)-proline, D-proline, or $β^3$-homoproline. The cyclic amino acid may be selected from cis-3-hydroxyproline, cis-4-hydroxyproline, cis-4-aminoproline, cis-4-fluoroproline, cis-4-chloroproline, cis-4-bromoproline, cis-4-methylproline, cis-4-ethylproline, cis-4-cyclohexyl-proline, cis-3-phenylproline, cis-4-phenylproline, cis-4-azidoproline, cis-4-carboxy-proline. The cyclic amino acid may be selected from trans-3-hydroxyproline, trans-4-hydroxyproline, trans-4-aminoproline, trans-4-fluoroproline, trans-4-chloroproline, trans-4-bromoproline, trans-4-methylproline, trans-4-ethylproline, trans-4-cyclohexyl-proline, trans-3-phenylproline, trans-4-phenylproline, trans-4-azidoproline, trans-4-carboxy-proline. The cyclic amino acid may be selected from 4-fluoroproline, 4-azidoproline, 3,4-dehydroproline, 4-hydroxyproline, 4,4-difluoroproline, azetidine-2-carboxylic acid, piperidine-2-carboxylic acid, 1,3-oxazolidine-4-carboxylic acid, or 1,3-thiazolidine-4-carboxylic acid. The cyclic amino acid may be (2S, 4S)-4-fluoro-L-proline, (2S, 4R)-4-fluoro-L-proline, (2S)-3,4-dehydro-L-proline, (2S, 4S)-4-hydroxy-L-proline, (2S, 4R)-4-hydroxy-L-proline, (2S)-4,4-difluoro-L-proline, (2S)-azetidine-2-carboxylic acid, (2S)-piperidine-2-carboxylic acid, or (4R)-1,3-thiazolidine-4-carboxylic acid. In some embodiments, the cyclic amino acid is cis-4-fluoroproline, trans-fluoroproline, cis-4-hydroxyproline, or trans-4-hydroxyproline.

The cyclic amino acid may be any one of the amino acids of Formulas I-XXVII:
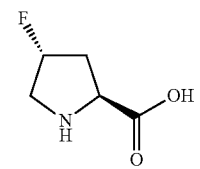
I
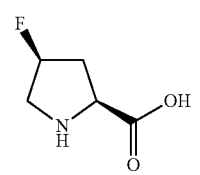
II
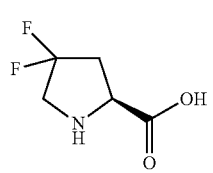
III
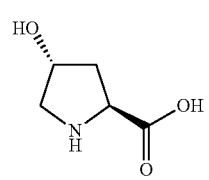
IV
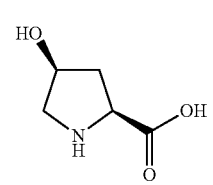
V
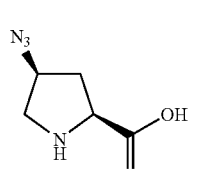
VI
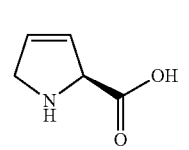
VII
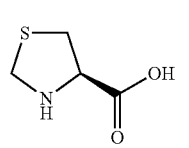
VIII
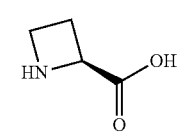
IX
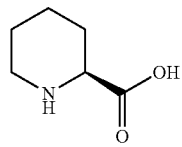
X
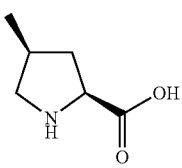
XI
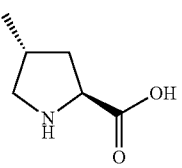
XII
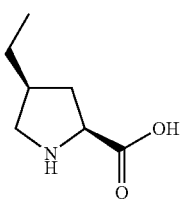
XIII
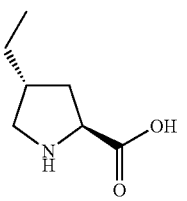
XIV
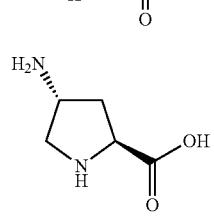
XV
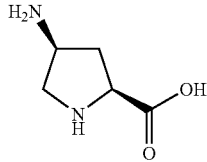
XVI
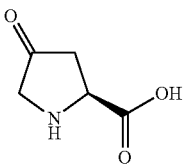
XVII
XVIII

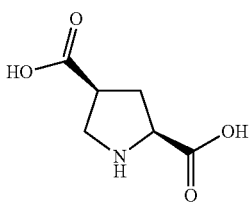

XIX

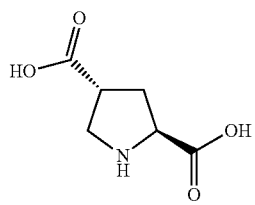

XX

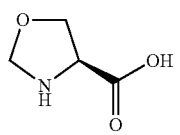

XXI

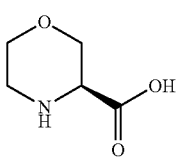

XXII

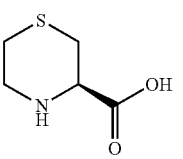

XXIII

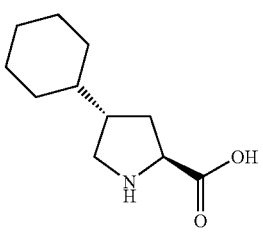

XXIV

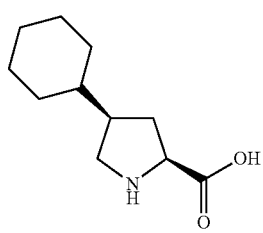

XXV

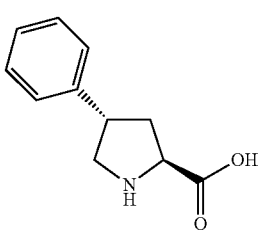

XXVI

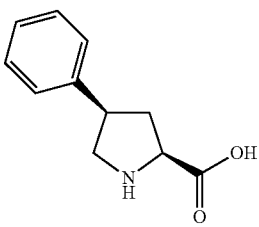

XXVII

Cyclic amino acids and methods for synthesizing cyclic amino acids are well known in the art (see, e.g., ROBERT M. WILLIAMS, SYNTHESIS OF OPTICALLY ACTIVE α-AMINO ACIDS (Pergamon Press 2013)). Additionally, many cyclic amino acids may be incorporated into recombinant proteins, e.g., instead of proline (see, e.g., NEDILJKO BUDISA, ENGINEERING THE GENETIC CODE 125 (Wiley-VCH 2006)).

Additionally, the cyclic amino acid may be a 1,2,3-triazole-modified proline, such as a substituted 4-(1H-1,2,3,-triazol-1-yl)-proline. The cyclic amino acid may have the structure of Formula XXVIII:

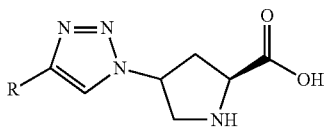

XXVIII wherein R represents hydrogen, alkyl, alkenyl, alkynyl, cycloalkyl, (cycloalkyl)alkyl, (heterocyclyl)alkyl, aralkyl, aryl, heteroaryl, heterocycloalkyl, silyl (e.g., trialkylsilyl or aryldialkylsilyl), or heteroaralkyl, where the alkyl, alkenyl, alkynyl, cycloalkyl, (cycloalkyl)alkyl, (heterocyclyl)alkyl, aralkyl, aryl, heteroaryl, heterocycloalkyl, silyl and heteroaralkyl groups are optionally substituted. In some embodiments, the cyclic amino acid has the structure of Formula XXVIII, wherein R is alkyl, substituted by a carboxylate group, e.g., at the terminal position of the alkyl, such as a $C_{12}$-$C_{18}$ alkyl, substituted by carboxylate (e.g., $(CH_2)_{15}COOH$). A 1,2,3-triazole-modified proline may be synthesized using the azide alkyne Huisgen cycloaddition, in which the azide of an azidoproline (e.g., cis-4-azidoproline or trans-4-azidoproline) and an alkyne undergo a 1,3-dipolar cycloaddition reaction (see, e.g., U.S. Pat. No. 8,575,095, hereby incorporated by reference). The nature of the alkyne is not particularly limiting, and the alkyne may be conjugated to an aromatic, alkyl, or acyl group, such as hexadecanedioic acid. In some embodiments, the 1,2,3-triazole-modified proline may comprise a polyethylene glycol moiety. The cyclic amino acid may be a substituted cis-4-(1H-1,2,3,-triazol-1-yl)-proline (e.g., cis-4-(4-R-1H-1,2,3,-triazol-1-yl)-proline, wherein R represents a substituted or unsubstituted alkyl, alkenyl, alkynyl, cycloalkyl, (cycloalkyl)alkyl, (heterocyclyl)alkyl, aralkyl, aryl, heteroaryl, heterocycloalkyl, silyl, or heteroaralkyl) or a substituted trans-4-(1H-1,2,3,-triazol-1-yl)-proline (e.g., trans-4-(4-R-1H-1,2,3,-triazol-1-yl)-proline, wherein R represents a substituted or unsubstituted alkyl, alkenyl, alkynyl, cycloalkyl, (cycloalkyl)alkyl, (heterocyclyl)alkyl, aralkyl, aryl, heteroaryl, heterocycloalkyl, silyl, or heteroaralkyl).

III. Peptides and Proteins Comprising Insulin Derivatives

In some aspects, the invention relates to a protein comprising an insulin derivative as described herein, or a peptide or protein comprising a subsequence of the insulin B chain. For example, the protein may be a precursor of an insulin derivative, such as a proinsulin derivative or a fusion protein.

In some embodiments, the invention relates to a peptide or protein comprising the sequence set forth in SEQ ID NO:3 (SGERGFFYTX$_1$X$_2$T); SEQ ID NO:4 (GERGFFYTX$_1$X$_2$T), SEQ ID NO:5 (ERGFFYTX$_1$X$_2$T), SEQ ID NO:6 (RGFFYTX$_1$X$_2$T), SEQ ID NO:7 (GFFYTX$_1$X$_2$T), SEQ ID NO:8 (FFYTX$_1$X$_2$T), SEQ ID NO:9 (FYTX$_1$X$_2$T), SEQ ID NO:10 (YTX$_1$X$_2$T), SEQ ID NO:11 (TX$_1$X$_2$T), or SEQ ID NO:12 (X$_1$X$_2$T), wherein at least one of X$_1$ and X$_2$ is a cyclic amino acid other than L-proline. In some embodiments, the amino acid at position X$_1$ is proline, lysine, aspartate, or glutamate, and the amino acid at position X$_2$ is the cyclic amino acid. For example, X$_1$ may be proline or lysine and X$_2$ may be the cyclic amino acid. In some embodiments, the amino acid at position X$_2$ is proline, lysine, aspartate, or glutamate, and the amino acid at position X$_1$ is the cyclic amino acid. For example, X$_2$ may be proline or lysine and X$_1$ may be the cyclic amino acid.

In some embodiments, the invention relates to a peptide or protein comprising the sequence set forth in SEQ ID NO:13 (SGERGFFYTX$_1$X$_2$), SEQ ID NO:14 (GERGFFYTX$_1$X$_2$), SEQ ID NO:15 (ERGFFYTX$_1$X$_2$), SEQ ID NO:16 (RGFFYTX$_1$X$_2$), SEQ ID NO:17 (GFFYTX$_1$X$_2$), SEQ ID NO:18 (FFYTX$_1$X$_2$), SEQ ID NO:19 (FYTX$_1$X$_2$), SEQ ID NO:20 (YTX$_1$X$_2$), or SEQ ID NO:21 (TX$_1$X$_2$), wherein at least one of X$_1$ and X$_2$ is a cyclic amino acid other than L-proline. In some embodiments, the amino acid at position X$_1$ is proline, lysine, aspartate, or glutamate, and the amino acid at position X$_2$ is the cyclic amino acid. For example, X$_1$ may be proline or lysine and X$_2$ may be the cyclic amino acid. In some embodiments, the amino acid at position X$_2$ is proline, lysine, aspartate, or glutamate, and the amino acid at position X$_1$ is the cyclic amino acid. For example, X$_2$ may be proline or lysine and X$_1$ may be the cyclic amino acid. In some embodiments X$_1$ is the cyclic amino acid and X$_2$ is deleted.

In some embodiments, the invention relates to a peptide or protein comprising the sequence set forth in SEQ ID NO:2. The peptide or protein may further comprise SEQ ID NO:1. In embodiments in which the peptide or protein comprises SEQ ID NO:1, the portion of the peptide or protein comprising SEQ ID NO:1 may be connected to the portion of the peptide or protein comprising SEQ ID NO:2 by a peptide bond (e.g., as in proinsulin) or by a disulfide bond (e.g., as in insulin).

In some embodiments, the peptide or protein further comprises a signal peptide. The signal peptide may be, for example, the sequence set forth in SEQ ID NO:22 (MALWMRLLPLLALLALWGPDPAAA). The peptide and protein may comprise the human insulin preform sequence, e.g., comprising substitutions as described herein (SEQ ID NO:23; MALWMRLLPLLALLALWGPDPAAAFVNQH LCGSHLVEALYLVCGERGFFYTX$_1$X$_2$TRR EAEDLQV GQVELGGGPGAGSLQPLALEGSLQKRGIVEQC-CTSICSLYQLENYCN).

The peptide or protein may comprise at least one affinity tag, e.g., for purification, such as AviTag, Calmodulin-tag, polyglutamate tag, E-tag, FLAG-tag, HA-tag, His-tag, Myc-tag, S-tag, SBP-tag, Softag 1, Softag 3, Strep-tag, TC tag, V5 tag, VSV-tag, Xpress tag, Isopeptag, and/or SpyTag. In some embodiments, the peptide comprises a His-tag.

In some embodiments, the peptide or protein comprises a protease cleavage site, e.g., for removing an affinity tag, chaperone, and/or signal peptide, such as a protease cleavage site for cleavage by enteropeptidase, Factor Xa, rhinovirus 3C protease, TEV protease, or thrombin. In some embodiments, the peptide or protein comprises an arginine and/or lysine, e.g., for cleavage with trypsin. In some embodiments, the peptide or protein comprises a methionine, e.g., for removing an affinity tag or chaperone by hydrolysis with cyanogen bromide.

IV. Methods for Producing Insulin Derivatives

In the human pancreas, insulin is synthesized as a single-chain preproinsulin precursor, consisting of a leader sequence followed by an A chain (21 residues) and a B chain (30 residues) linked by a connecting C-peptide (35 residues). The A and B chain are linked by two inter-chain disulfide bridges (A7-B7 and A20-B19). There is also an intra-A chain disulfide bridge between cysteine residues at A6 and A11. Subsequent proteolysis of proinsulin by a trypsin-like enzyme removes the C-peptide to yield a mature, active insulin. The main bottlenecks in recombinant insulin expression are centered on achieving robust post-translational processing of proinsulin, including proteolysis, the correct folding of the protein, and the formation of the inter-chain disulfide bridges. These steps have to be carefully controlled to ensure optimal activity of the purified, mature insulin.

Robust production processes for expression of insulin in *E. coli* are known in the art (see, e.g., Jonasson, *Eur. J. Biochem.* 236:656-661 (1996); Cowley, *FEBS Lett.* 402: 124-130 (1997); Cho, *Biotechnol. Bioprocess Eng.* 6:144-149 (2001); Tikhonov, *Protein Exp. Pur.* 21:176-182 (2001); Malik, *Protein Exp. Pur* 55:100-111 (2007); Min, *J. Biotech.* 151:350-356 (2011)). In the most common process, the protein is expressed as a single-chain proinsulin construct with a fusion protein or affinity tag. This approach results in good overall yield and reduces experimental complexity by decreasing the number of intermediate processing steps, while also ensuring that refolding results in a native-like insulin (see, e.g., Jonasson, *Eur. J. Biochem.* 236:656-661 (1996); Cho, *Biotechnol. Bioprocess Eng.* 6:144-149 (2001); Tikhonov, *Protein Exp. Pur.* 21:176-182 (2001); Min, *J. Biotech.* 151:350-356 (2011)). When expressed in *E. coli*, proinsulin is usually found in inclusion bodies. By choosing appropriate strains and expression vectors, this strategy enables high expression and minimal proteolysis. Insulin may also be expressed via periplasmic and secretory routes. Advantageously, *E. coli* hosts are also well-suited for incorporating noncanonical amino acids, such as cyclic amino acids, into proteins.

A. Methods Related to the Expression of Recombinant Peptides and Proteins

In some aspects, the invention relates to a method of expressing any one of the peptides, proteins, and/or insulin derivatives described herein in a cell. The method may comprise incubating the cell in a medium comprising a cyclic amino acid, e.g., wherein the cyclic amino acid is not L-proline. The medium may nevertheless comprise proline, because proline often cannot be completely removed from a cell culture and because a cyclic amino acid may not completely compensate for a cell's proline requirements.

In some embodiments, the cell is a bacterium, yeast, fungal cell, plant cell, insect cell, or mammalian cell. Suitable expression cells include *Escherichia coli, Bacillus subtilis, Pseudomonas fluorescens, Leishmania tarentolae, Saccharomyces cerevisiae, Pichia Pastoris, Nicotiana, Drosophila melanogaster, Spodoptera frugiperda, Trichoplusia ni, Gallus gallus, Mus musculus, Sus scrofa, Ovis aries, Capra aegagrus, Bos taurus,* Sf9 cells, Sf21 cells, Schneider 2 cells, Schneider 3 cells, High Five cells, NS0 cells, Chinese Hamster Ovary ("CHO") cells, Baby Hamster Kidney cells, COS cells, Vero cells, HeLa cells, and HEK 293 cells. In some preferred embodiments, the cell is an *Escherichia coli, Saccharomyces cerevisiae*, or CHO cell. The cell may be *Escherichia coli*.

B. Methods Related to the Synthesis of Peptides Comprising a Cyclic Amino Acid

In some aspects, the invention relates to a method of synthesizing any one of the peptides, proteins, and/or insulin derivatives described herein. The method may comprise synthesizing a peptide or protein comprising SEQ ID NO:3 (SGERGFFYTX$_1$X$_2$T); SEQ ID NO:4 (GERGFFYTX$_1$X$_2$T), SEQ ID NO:5 (ERGFFYTX$_1$X$_2$T), SEQ ID NO:6 (RGFFYTX$_1$X$_2$T), SEQ ID NO:7 (GFFYTX$_1$X$_2$T), SEQ ID NO:8 (FFYTX$_1$X$_2$T), SEQ ID NO:9 (FYTX$_1$X$_2$T), SEQ ID NO:10 (YTX$_1$X$_2$T), SEQ ID NO:11 (TX$_1$X$_2$T), SEQ ID NO:12 (X$_1$X$_2$T), SEQ ID NO:13 (SGERGFFYTX$_1$X$_2$), SEQ ID NO:14 (GERGFFYTX$_1$X$_2$), SEQ ID NO:15 (ERGFFYTX$_1$X$_2$), SEQ ID NO:16 (RGFFYTX$_1$X$_2$), SEQ ID NO:17 (GFFYTX$_1$X$_2$), SEQ ID NO:18 (FFYTX$_1$X$_2$), SEQ ID NO:19 (FYTX$_1$X$_2$), SEQ ID NO:20 (YTX$_1$X$_2$), or SEQ ID NO:21 (TX$_1$X$_2$), wherein X$_1$ and X$_2$ are selected as described herein, supra. The peptide or protein may then be conjugated to the rest of an insulin B chain. For example, the method may comprise synthesizing the peptide set forth in SEQ ID NO:3 (SGERGFFYTX$_1$X$_2$T) or SEQ ID NO:13 (SGERGFFYTX$_1$X$_2$), and the method may further comprise ligating the peptide to a molecule comprising the insulin B chain N-terminus (e.g., SEQ ID NO:24; FVNQHLCG-SHLVEALYLV), e.g., by native chemical ligation.

In some embodiments, the method comprises synthesizing the insulin B chain, e.g., SEQ ID NO:2 or SEQ ID NO:32. The method may comprise synthesizing the insulin A chain, e.g., SEQ ID NO:1. Thus, the method may comprise synthesizing the insulin derivative.

c. Purification

The method may further comprise purifying and/or isolating the peptide or protein, e.g., by centrifugation, filtration, an affinity tag, and/or chromatography, such as ion exchange chromatography, size exclusion chromatography, affinity chromatography, or HPLC.

V. Pharmaceutical Formulations Comprising an Insulin Analog

In some aspects, the invention relates to a composition comprising an insulin analog as described herein. The composition may be formulated for injection, e.g., the composition may be a liquid. The composition may be formulated for injection into a subject, such as a human subject. The composition may be sterile. The composition may be a pharmaceutical composition, such as a sterile, injectable pharmaceutical composition. The composition may be formulated for subcutaneous injection. In some embodiments, the composition is formulated for transdermal, intradermal, transmucosal, nasal, inhalational, intramuscular, or enteral administration. The composition may be formulated in an oral dosage form or a pulmonary dosage form.

The composition may comprise an insulin analog, as described herein, in a pharmaceutically acceptable carrier. As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions.

Pharmaceutically acceptable diluents include saline and aqueous buffer solutions. Pharmaceutical compositions suitable for injection include sterile aqueous solutions (where water soluble) or dispersions and sterile powders for the extemporaneous preparation of sterile injectable solutions or dispersions. Isotonic agents, for example, sugars, polyalcohols such as mannitol and sorbitol, and/or sodium chloride may be included in the pharmaceutical composition. In all cases, the composition should be sterile and should be fluid. It should be stable under the conditions of manufacture and storage and must include preservatives that prevent contamination with microorganisms, such as bacteria and fungi. Dispersions can also be prepared in glycerol, liquid polyethylene glycols, and mixtures thereof and in oils. Under ordinary conditions of storage and use, these preparations may contain a preservative to prevent the growth of microorganisms.

The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants.

Prevention of the action of microorganisms in the pharmaceutical composition can be achieved by various antibacterial and antifungal agents, for example, parabens, chlorobutanol, phenol, o-cresol, m-cresol, p-cresol, chlorocresol, resorcinol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorhexidine, sodium dehydroacetate, ethyl p-hydroxybenzoate, benzethonium chloride, chlorphenesine (3p-chlorphenoxypropane-1, 2-diol), ascorbic acid, thimerosal, and the like. In some preferred embodiments, the composition comprises phenol and/or m-cresol.

In some preferred embodiments, the pharmaceutical composition comprises zinc, i.e., $Zn^{2+}$ (see, e.g., U.S. Pat. No. 9,034,818; U.S. Patent Publication Application No. 2015/0126442, hereby incorporated by reference). In some embodiments, the pharmaceutical composition may comprise zinc at a ratio to the insulin derivative of about 1:6, about 1:5, about 1:4, about 1:3, about 1:2, about 2:3, about 5:6, about 1:1, about 7:6, about 4:3, about 9:6, about 5:3, about 11:6, or about 2:1 (mole:mole).

Compositions may be formulated in dosage unit form for ease of administration and uniformity of dosage. Dosage unit form refers to physically discrete units suited as unitary dosages for a mammalian subject; each unit contains a predetermined quantity of active material (e.g., the insulin analog) calculated to produce the desired therapeutic effect, in association with the required pharmaceutical carrier. The specification for the dosage unit forms of the invention are dictated by and directly dependent on (a) the unique characteristics of the active material and the particular therapeutic effect to be achieved, and (b) the limitations inherent in the art of compounding such an active compound for the treatment of, and sensitivity of, individual subjects.

For lung instillation, aerosolized solutions are used. In sprayable aerosol preparations, the active protein may be in combination with a solid or liquid inert carrier material. The compositions may also be packaged in a squeeze bottle or in admixture with a pressurized volatile, normally gaseous propellant. The aerosol preparations can contain solvents, buffers, surfactants, and antioxidants in addition to the insulin analog of the invention.

The pharmaceutical composition may further comprise a second insulin derivative, wherein the second insulin derivative does not comprise the cyclic amino acid. For example, the second insulin derivative may comprise L-proline instead of the cyclic amino acid. The second insulin derivative may comprise the same amino acid sequence as the insulin derivative except for the substitution of the cyclic amino acid with L-proline. Thus, the second insulin derivative may be wild type insulin, i.e., comprising L-proline at the insulin B chain B28 position and lysine at the insulin B chain B29 position. The composition may comprise, for example, the insulin derivative and the second insulin derivative at a ratio of about 9:1 (mole:mole) or higher.

VI. Methods of Treating Disease or Condition a. Methods Comprising Administering an Insulin Derivative In some aspects, the invention relates to a method for treating a disease or condition in a subject, comprising administering to the subject a composition comprising an insulin derivative as described herein. In some aspects, the invention relates to a method for treating a disease or condition in a subject, comprising administering to the subject a pharmaceutical composition as described herein. The disease or condition may be hyperglycemia, type 2 diabetes, impaired glucose tolerance, type 1 diabetes, obesity, metabolic syndrome X, or dyslipidemia.

Administering the composition may comprise any suitable means of delivering a peptide, protein, or insulin derivative. Administering a composition preferably comprises parenteral administration. In some preferred embodiments, the composition is administered by subcutaneous injection. In some preferred embodiments, the composition is administered by inhalation. Administering an insulin derivative may comprise transdermal, intradermal, transmucosal, nasal, intramuscular, or enteral administration.

b. Subjects

The subject may be any species of organism that naturally produces insulin. In some embodiments, the subject is selected from murines, felines, canines, ovines, porcines, bovines, equines, and primates. For example, the subject may be selected from *Felis catus, Canis lupus familiaris*, and *Homo sapiens*. The subject may or may not have diabetes. In some embodiments, the subject has type 1 diabetes mellitus. The subject may have type 2 diabetes mellitus. The subject may have gestational diabetes. The subject may have hyperglycemia. The subject may have a blood glucose level higher than 5.6 mmol/L, such as higher than 7 mmol/L or higher than 11.1 mmol/L. The subject may have hyperglycemia, type 2 diabetes, impaired glucose tolerance, type 1 diabetes, obesity, metabolic syndrome X, or dyslipidemia.

EXEMPLIFICATION

The present description is further illustrated by the following examples, which should not be construed as limiting in any way. The contents of all cited references (including literature references, issued patents, and published patent applications) are hereby expressly incorporated by reference. When definitions of terms in documents that are incorporated by reference herein conflict with those used herein, the definitions used herein govern.

Example 1

Design of an Expression Construct

Figure 2:
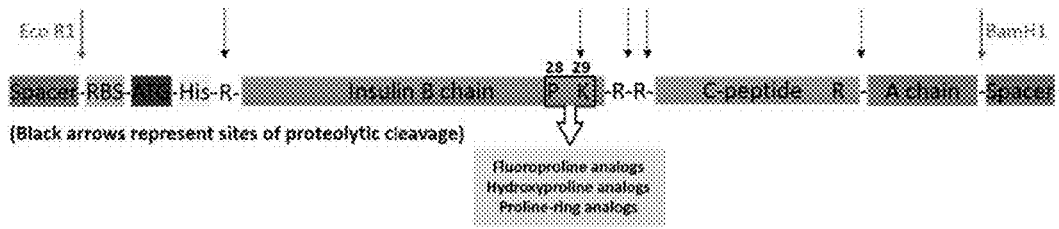
FIG. 2 depicts an expression construct comprising a leader peptide (ATG-His-R), B chain, C-peptide, and A chain. The expression construct comprises a 5' EcoR1restriction site and a 3' BamH1 restriction site for molecular cloning. "RBS" represents the ribosome binding site. "R" represents arginine, which allows for cleavage with trypsin. Cyclic amino acids may be incorporated into the insulin B chain at position B28 (labeled "P" for proline) or position B29 (labeled "K" for lysine).

An expression construct was designed, which comprises a short leader sequence, a hexahistidine tag (His-Tag), and a basic amino acid, arginine, as a linker between the leader peptide and the B-chain (FIG. 2). This construct enables single-step proteolytic cleavage of the C-peptide and the leader sequence. The C-peptide comprises an Arg-Arg dibasic linker at the N-terminus and an Arg residue at the C-terminus for proteolytic cleavage. This C-peptide differs from the native human C-peptide sequence by substitution of Lys at position 64 as described by Jonasson et. al (*Eur. J. Biochem.* 236:656-661 (1996)).

Example 2

Expression of Insulin Derivatives Comprising Cyclic Amino Acids

A small library of proline analogs are introduced into insulin at positions 28 and 29 of the B-chain of human insulin. Specifically, 4-fluoroproline, 4-azidoproline, 3,4-dehydroproline, 4-hydroxyproline, 4,4-difluoroproline, azetidine-2-carboxylic acid, piperidine-2-carboxylic acid, 1,3-oxazolidine-4-carboxylic acid, and 1,3-thiazolidine-4-carboxylic acid are each independently introduced. Fluorinated analogues change the cis-trans isomerization tendencies of proline residues, and fluorinated analogs of other amino acids have been used to alter the folding, stability, solubility and aggregation properties of proteins (Link, *Curr. Opin. Biotechnol.* 14:603-609 (2003); Johnson, *Curr. Opin. Chem Biol.* 14:774-780 (2010)). Many of these analogs have shown good translational activity in *E. coli* cells (Kim, *Chem Bio Chem* 5:928-936 (2004)). Mature human insulin comprises only one proline residue (at position B28), and thus, the replacement of L-proline with different cyclic amino acids is unlikely to significantly affect the expression of insulin derivatives.

Figure 3:
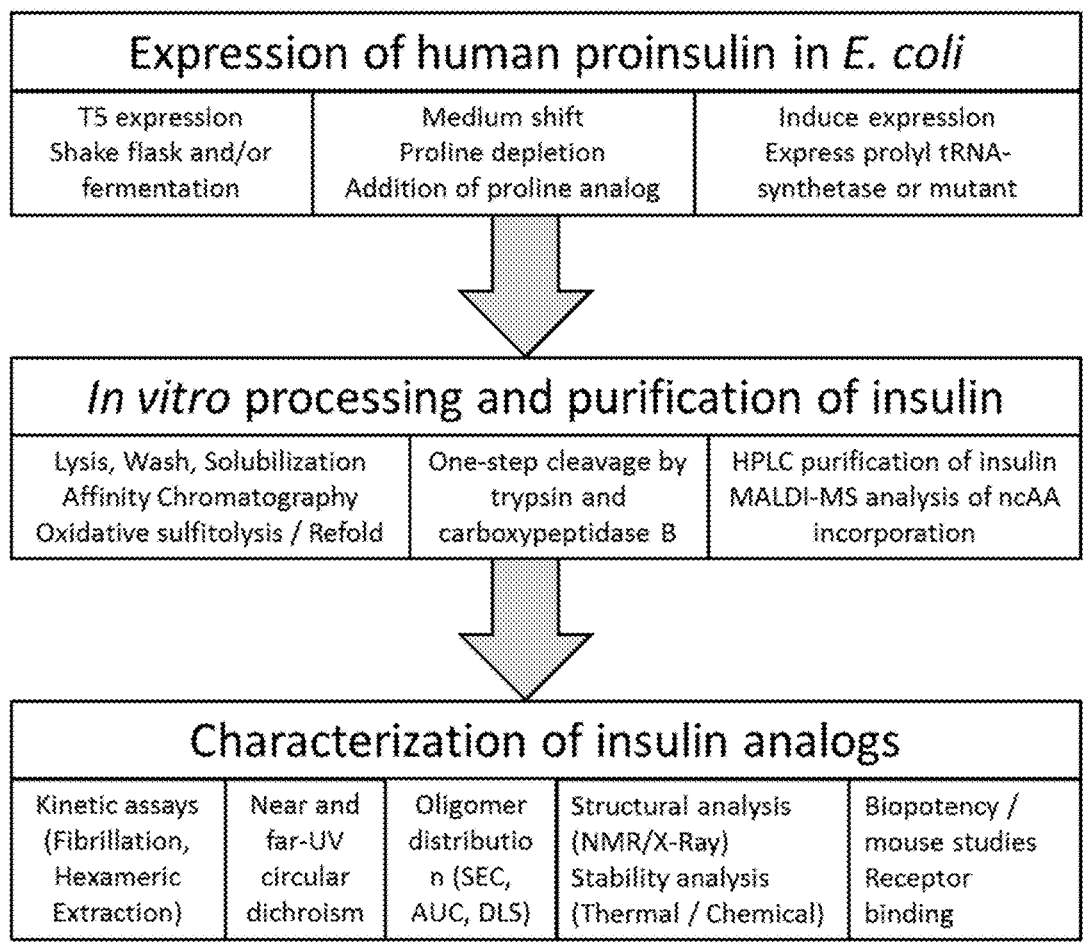
FIG. 3 is a flowchart that summarizes steps in the preparation and characterization of insulin derivatives.

Insulin analogs are expressed, folded and purified according to well-established and optimized protocols (see, e.g., Jonasson, *Eur. J. Biochem.* 236:656-661 (1996); Cho, *Biotechnol. Bioprocess Eng.* 6:144-149 (2001); Tikhonov, *Protein Exp. Pur.* 21:176-182 (2001); Min, *J. Biotech.* 151:350-356 (2011)). Briefly, cells are lysed following batch expression and subjected to centrifugation to isolate inclusion bodies. Pellets containing inclusion bodies are washed thoroughly in Tris buffers. Proinsulin variants are solubilized and converted to their hexasulfonate derivatives by oxidative sulfitolysis. Following this step, the protein is diluted into refolding buffer to induce disulfide bond formation. After refolding, proinsulin derivatives ate purified via metal affinity chromatography. Purified fusion proteins are collected, lyophilized, and further purified by size-exclusion chromatography. One-step trypsin and carboxypeptidase B cleavage yields mature insulin. As an alternative approach, one-step cleavage using Alp protease may be used. A final purification of the cleaved products is accomplished by reverse phase high performance liquid chromatography (RP-HPLC) to yield pure samples of mature insulin and its analogs. The overall expression, purification, and refolding strategy is shown in FIG. 3.

Example 3

Figure 4:
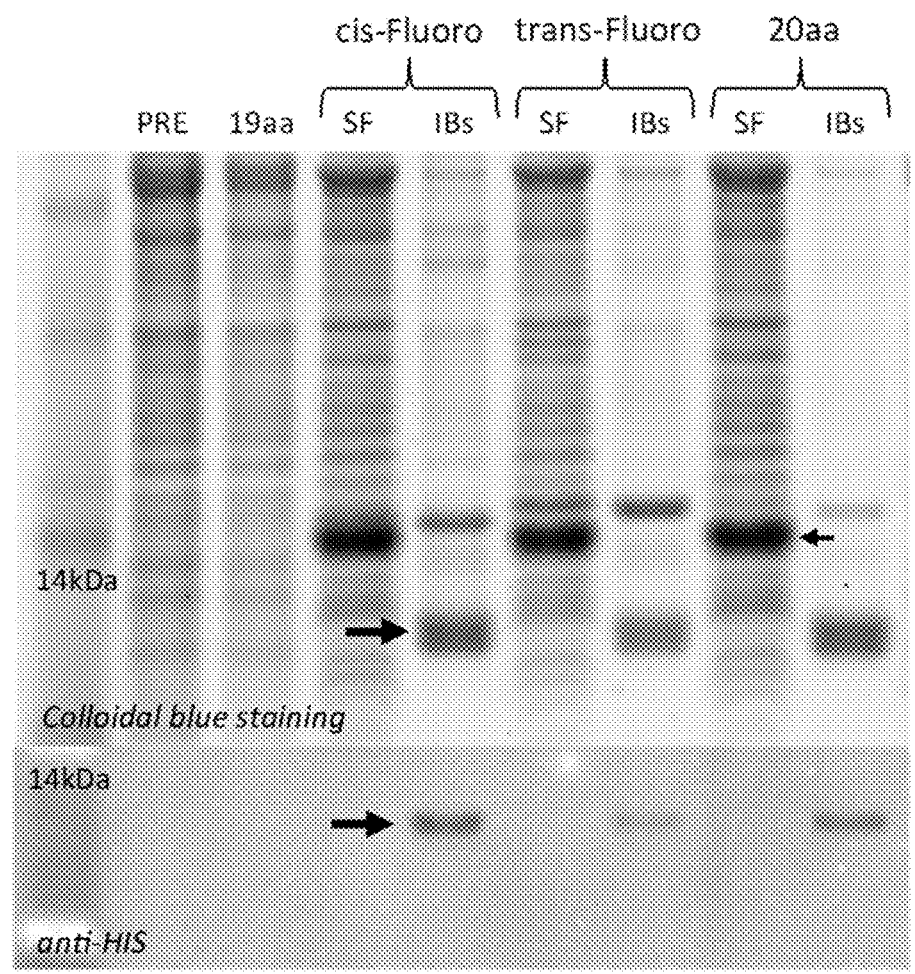
FIG. 4 depicts a polyacrylamide gel of protein from *E. coli* grown in media comprising either cis-4-fluorproline ("cis-Fluoro"") or trans-4-fluoroproline ("trans-Fluoro"). Lanes labeled "SF" correspond to protein recovered from the soluble fraction of the culture (i.e., the cytosol), and lanes labeled "IBs" correspond to protein recovered from inclusion bodies. The proinsulin derivatives display bands in the inclusion body lanes with molecular weights of less than 14 kDa, as depicted by colloidal blue staining The identities of these bands were confirmed by Western blotting, using an anti-polyhistidine antibody.

Expression of Proinsulin Derivatives Comprising Cis-4-Fluorproline, Trans-4-Fluoroproline, and 4-Hydroxyproline Proinsulin derivatives were expressed in *E.coli* in media comprising either cis-4-fluoroproline, trans-4-fluoroproline, or 4-hydroxyproline, as described in Example 2. A strong proinsulin band was observed in inclusion bodies, as detected by polyacrylamide gel electrophoresis (FIG. 4). The identity of the proinsulin bands was confirmed by Western blotting (FIG. 4).

Example 4

Expression and Folding of Proinsulin Comprising 4-Hydroxyproline

Figure 5:
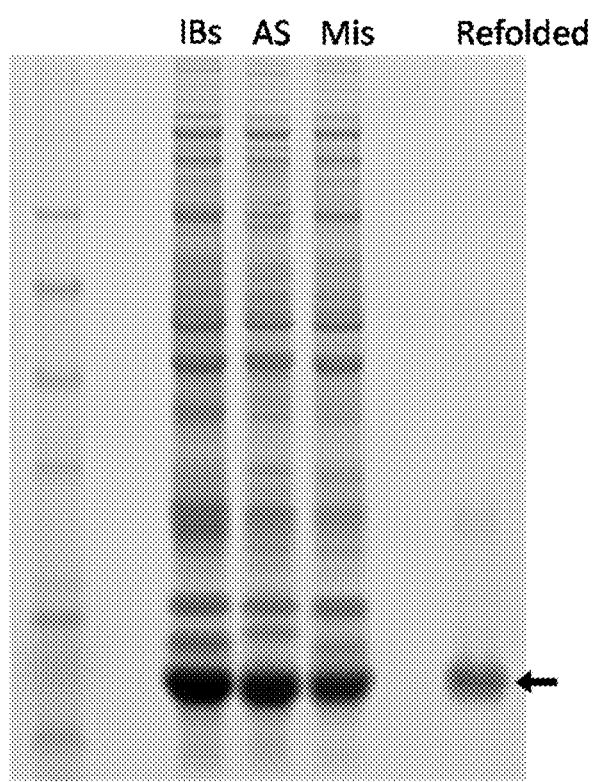
FIG. 5 depicts a polyacrylamide gel of insulin expressed in *E. coli* grown in media comprising 4-hydroxyproline. The lanes labeled "IBs" correspond to protein recovered from inclusion bodies, the lane labeled "AS" corresponds to protein recovered from inclusion bodies after sulfitolysis, the lane labeled "Mis" corresponds to misfolded proinsulin, and the lane labeled "Refolded" corresponds to properly folded proinsulin, which displays a single band that is marked with an arrow.

Proinsulin derivatives were expressed in *E. coli* in media comprising 4-hydroxyproline, as described in Example 2. Proinsulin was refolded following a sulfitolysis protocol to ensure the proper formation of disulfide bonds. Purified, refolded proinsulin was analyzed by polyacrylamide gel electrophoresis, along proinsulin fractions from other steps of the refolding method (FIG. 5).

Example 5

Yields for Incorporating Cyclic Amino Acids into Proinsulin

Insulin derivatives were expressed in proline-auxotrophic *E. coli* and processed using the strategy outlined in Example 1 in media supplemented with one of L-proline, (2S, 4S)-4-fluoro-L-proline, (2S, 4R)-4-fluoro-L-proline, (2S)-3,4-dehydro-L-proline, (2S, 4S)-4-hydroxy-L-proline, (2S, 4R)-4-hydroxy-L-proline, (2S,4S)-4-azido-L-proline, (2S)-4,4-difluoro-L-proline, (2S)-azetidine-2-carboxylic acid, (2S)-piperidine-2-carboxylic acid, and (4R)-1,3-thiazolidine-4-carboxylic acid. The insulin gene comprised the wild type sequence, for incorporation of cyclic amino acids into the insulin B chain B28 position (SEQ ID NO:26). Protein concentrations were measured using the bicinchoninic acid ("BCA") assay (Table 1).

TABLE 1

Yields and Incorporation of Cyclic Amino Acids into Proinsulin

| # | Name | Yield[1,2] | Incorporation[3] |
|---|------|-----------|------------------|
| 1 | L-proline | 40 mg/L[4] | — |
| 2 | (2S,4S)-4-fluoro-L-proline | 35 mg/L | 93% (+18 Da) |
| 3 | (2S,4R)-4-fluoro-L-proline | 22 mg/L | 86% (+18 Da) |
| 4 | (2S)-3,4-dehydro-L-proline | 19 mg/L | 100% (−2 Da) |
| 5 | (2S,4S)-4-hydroxy-L-proline | 18 mg/L | 89% (+16 Da) |
| 6 | (2S,4R)-4-hydroxy-L-proline | 32 mg/L[5] | 86% (+16 Da) |
| 7 | (2S)-4,4-difluoro-L-proline | 12 mg/L | 91% (+36 Da) |
| 8 | (2S)-azetidine-2-carboxylic acid | 14 mg/L | 100% (−14 Da) |
| 9 | (2S)-piperidine-2-carboxylic acid | 11 mg/L | 86% (+14 Da) |
| 10 | (4R)-1,3-thiazolidine-4-carboxylic acid | 28 mg/L[5] | 89%(+18 Da) |

[1]Estimated using BCA assay, soluble proinsulin after purification and refolding
[2]Unless otherwise noted, yield is calculated from 100 mL cultures
[3]Quantified using MALDI-MS
[4]From 6 L culture volume, using rich media and prototrophic *E. coli*
[5]From 1 L culture volume, using minimal media and proline-auxotrophic *E. coli*

Figure 6:
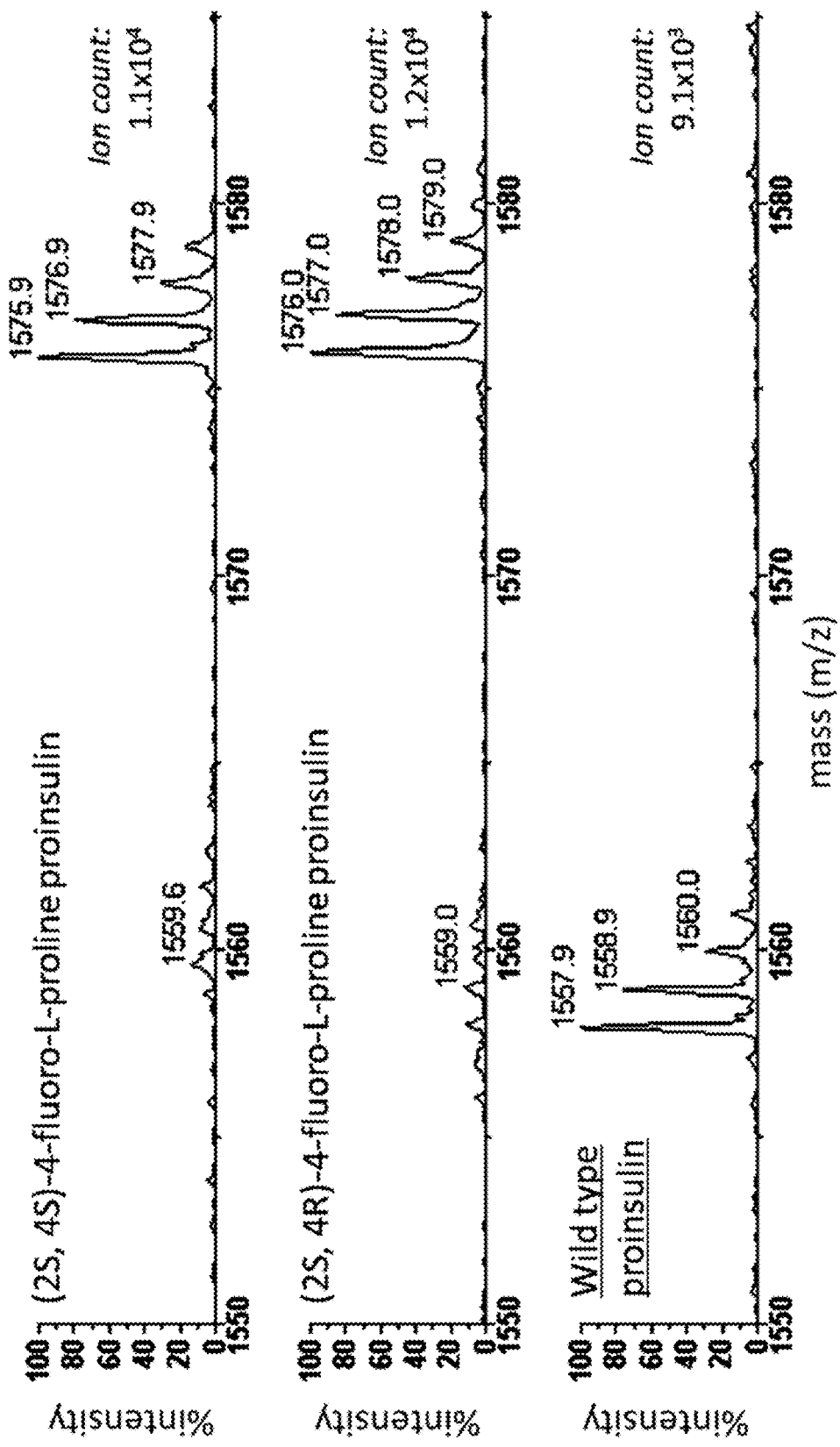
FIG. 6 shows MALDI-MS spectra for proinsulin derivatives. The native proinsulin peptide RGFFYTPKTRRE (SEQ ID NO:25) has a molecular weight of 1558 amu. The (2S, 4S)-4-fluoro-L-proline derivative has an expected atomic mass of 1575 amu. The (2S, 4R)-4-fluoro-L-proline derivative has an expected atomic mass of 1575 amu. The (2S)-3,4-dehydro-L-proline derivative has an expected atomic mass of 1556 amu. The (4R)-1,3-thiazolidine-4-carboxylic acid derivative has an expected atomic mass of 1576 amu. The (2S, 4S)-4-hydroxy-L-proline derivative has an expected atomic mass of 1574 amu. The (2S, 4R)-4- hydroxy-L-proline derivative has an expected atomic mass of 1574 amu. The (2S)-4,4-difluoro-L-proline derivative has an expected atomic mass of 1593 amu. The (2S)-azetidine-2-carboxylic acid derivative has an expected atomic mass of 1544 amu. The (2S)-piperidine-2-carboxylic acid derivative has an expected atomic mass of 1572 amu. The (2S,4S)-4-azido-L-proline derivative has an expected atomic mass of 1599 amu, and it is expected to display an amino peak at 1573 amu as well. Each cyclic amino acid was incorporated into the insulin B chain B28 position.
Figure 6:
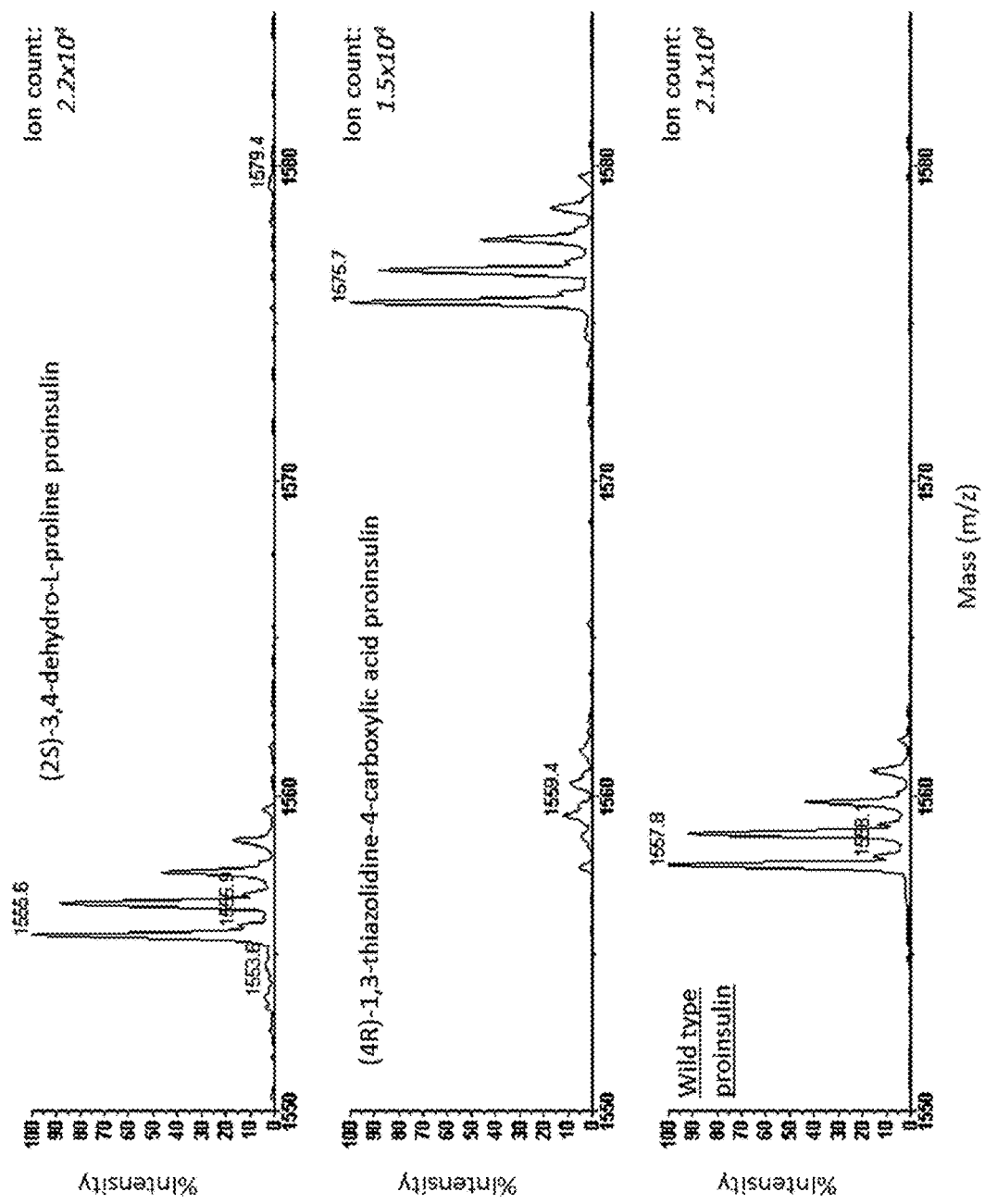
Figure 6:
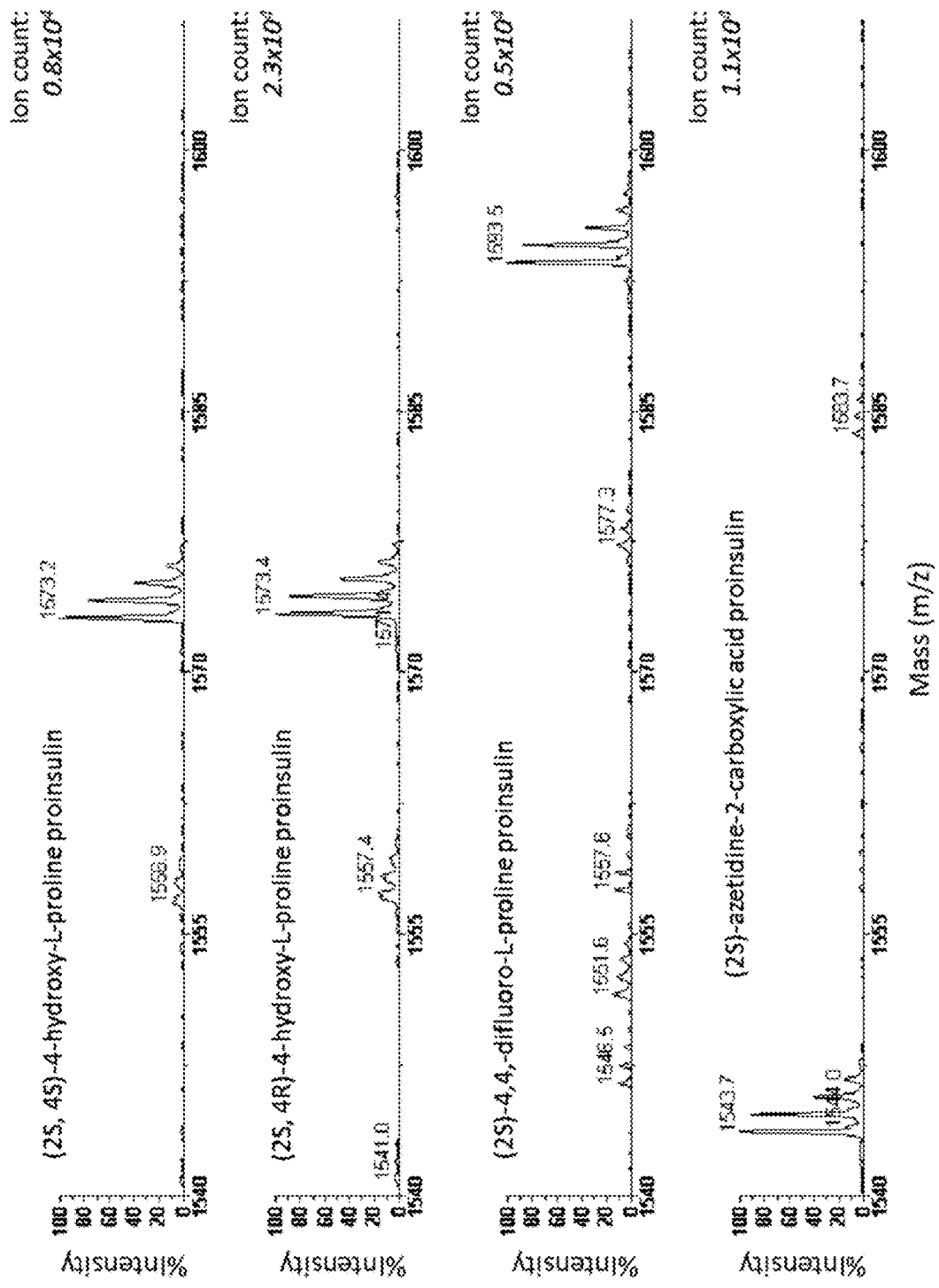
Figure 6:
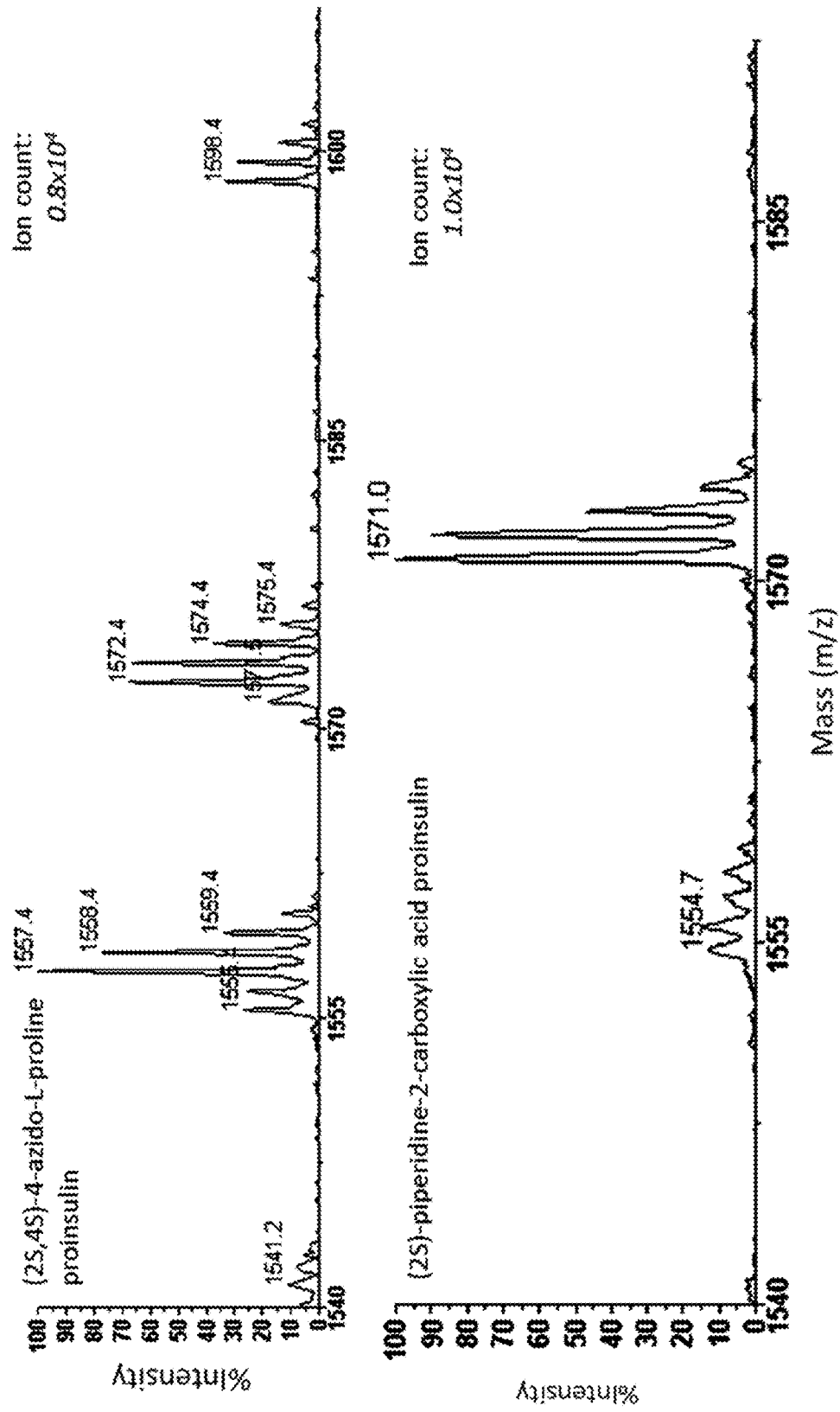

The incorporation rate of each cyclic amino acid was determined by MALDI-MS on the proinsulin form of each insulin derivative. Briefly, each proinsulin derivative was precipitated with acetone and re-dissolved in a urea buffer. The protein was reduced, alkylated, and then digested with Glu-C. The peptides were purified with a C18 ziptip and analyzed by MALDI-MS. Glu-C digestion results in a 1557.8 amu peptide (SEQ ID NO:25; RGFFYTPKTRRE), for wild type insulin comprising insulin B chain B28 and B29 residues. The incorporation rate for each cyclic amino acid was approximated by monitoring ion counts for peptides with a mass corresponding to the cyclic amino acid relative to the ion counts at 1557.8 amu, for wild type insulin (FIG. 6).

Example 6

HPLC Purification of Mature Insulin

Wild type proinsulin and a proinsulin comprising (2S, 4R)-4-hydroxy-L-proline in the insulin B chain B28 position were cleaved with trypsin and carboxypeptidase B at 37° C. for 1-2 hours. The mature insulins were purified by reverse phase HPLC using a preparative C18 column (Advanced Chromatography Technologies, Aberdeen, Scotland) and an acetonitrile gradient from 0% to 39% over 55 minutes. The insulin derivative comprising (2S, 4R)-4-hydroxy-L-proline in the insulin B chain B28 position displayed a similar elution profile relative to wild type insulin (FIG. 7).

The mature wild type and (2S, 4R)-4-hydroxy-L-proline insulins were analyzed by MALDI-MS as described above and compared with MALDI-MS spectra for insulin lispro, insulin aspart, and laboratory grade insulin (Sigma-Aldrich, St. Louis, Mo.) (FIG. 8).

Example 7

Tertiary Structure of Insulin Derivatives

The structures on insulin derivatives comprising (2S, 4S)-4-hydroxy-L-proline, (2S, 4R)-4-hydroxy-L-proline, or (4R)-1,3-thiazolidine-4-carboxylic acid at the insulin B chain B28 position were assessed by circular dichroism ("CD") spectroscopy, and the spectra of the insulin derivatives were compared to spectra for wild type insulin and insulin lispro (FIG. 9). Each insulin derivative and the wild type and insulin lispro controls were dissolved at 0.6 mM in tris buffer, pH 8. Notably, the (2S, 4R)-4-hydroxy-L-proline derivative displayed a CD spectrum that was much more similar to insulin lispro than wild type insulin, suggesting that the substitution of proline at position B28 with (2S, 4R)-4-hydroxy-L-proline favors a monomeric state. Additionally, the (4R)-1,3-thiazolidine-4-carboxylic acid derivative displayed a negative band at 208 nm that was slightly greater in magnitude than wild type insulin, and each insulin derivative displayed a negative band at 222 nm that was smaller in magnitude than wild type insulin.

The tertiary structures of insulin derivatives comprising (2S, 4S)-4-hydroxy-L-proline, (2S, 4R)-4-hydroxy-L-proline, or (4R)-1,3-thiazolidine-4-carboxylic acid at the insulin B chain B28 position were further assessed by analytical ultracentrifugation. Each insulin derivative and wild type and insulin aspart controls were dissolved at 0.6 mM in tris buffer, pH 8. Notably, the oligomerization of the (2S, 4R)-4-hydroxy-L-proline insulin derivative was indicative of a shift toward a monomeric state (FIG. 10).

Example 7

Thermostability of Insulin Derivatives

The stability of insulin derivatives comprising (2S, 4S)-4-hydroxy-L-proline, (2S, 4R)-4-hydroxy-L-proline, or (4R)-1,3-thiazolidine-4-carboxylic acid at the insulin B chain B28 position was assessed by circular dichroism ("CD") spectroscopy, and the thermal melts of insulin derivatives were compared to thermo melts for wild type insulin and insulin lispro (FIG. 11). The (2S, 4R)-4-hydroxy-L-proline insulin derivative displayed a melting curve that was similar to insulin lispro. The (2S, 4S)-4-hydroxy-L-proline and (4R)-1,3-thiazolidine-4-carboxylic acid insulin derivatives displayed melting curves that were similar to wild type insulin.

Example 8

Biological Activity of Insulin Derivatives

The biological activities for insulin derivatives were confirmed for insulin derivatives comprising (2S, 4S)-4-hydroxy-L-proline, (2S, 4R)-4-hydroxy-L-proline, or (4R)-1,3-thiazolidine-4-carboxylic acid at the insulin B chain B28 position using an insulin receptor phosphorylation assay as described by Wharton, J. et al. (J. Biol. Chem. 280(14): 13483 (2005)). Briefly, HEK293 cells were treated with 200 nM of each insulin derivative and wild type insulin, or 20 nM of wild type insulin, whole cell lysates were run on a SDS-PAGE gel, and total inulin receptor and phosphorylated insulin receptor were detected by western blotting. FIG. 12 shows that each of the (2S, 4S)-4-hydroxy-L-proline, (2S, 4R)-4-hydroxy-L-proline, and (4R)-1,3-thiazolidine-4-carboxylic acid insulin derivatives were capable driving phosphorylation of the insulin receptor at levels similar to wild type insulin. Additionally, each of the insulin derivatives was capable of driving more phosphorylation than the lower concentration (0.1×; 20 nM) of wild type insulin. These results suggest that the substitution of L-proline at the insulin B chain B28 position with a different cyclic amino acid does not affect insulin activity.

Example 9

Generation of 1,2,3-Triazole-modified Prolines

Proinsulin derivatives were expressed in *E. coli* in media comprising either L-proline or (2S,4S)-4-azido-L-proline, as described in Example 2. The cells were lysed, and TAMRA-alkyne was clicked to cell lysates. The modified cell lysates were run on a polyacrylamide gel, which was visualized for TAMRA. TAMRA imaging revealed a strong band with an apparent molecular weight that corresponds to the molecular weight of the proinsulin construct for the azidoproline lysate and no band for the L-proline lysate, suggesting that the TAMRA alkyne reacted specifically with the azidoproline (FIG. 13).

EQUIVALENTS

Those skilled in the art will recognize, or be able to ascertain using no more than routine experimentation, many equivalents to the specific embodiments of the invention described herein. Such equivalents are intended to be encompassed by the following claims.

INCORPORATION BY REFERENCE

Each of the patents, published patent applications, and other references described herein is hereby incorporated by reference in its entirety.

---

What is claimed:

1. An insulin derivative, comprising a cyclic amino acid at position B28, wherein the cyclic amino acid is (2S, 4S)-4-hydroxy-L-proline, (2S, 4S)-4-fluoro-L-proline, (2S)-piperidine-2-carboxylic acid, (2S)-4,4-difluoro-L-proline, or (4R)-1,3-thiazolidine-4-carboxylic acid.

2. The insulin derivative of claim 1, wherein the cyclic amino acid is (2S, 4S)-4-fluoro-L-proline, (2S)-4,4-difluoro-L-proline, (2S)-piperidine-2-carboxylic acid, or (4R)-1,3-thiazolidine-4-carboxylic acid.

3. The insulin derivative of claim 1, wherein the insulin A chain comprises the sequence set forth in SEQ ID NO:1.

4. The insulin derivative of claim 1, wherein the insulin B chain comprises the sequence set forth in SEQ ID NO:2 or SEQ ID NO:32, wherein X1 corresponds to position B28 and X2 corresponds to position B29.

5. The insulin derivative of claim 1, wherein the amino acid at position B29 is proline, lysine, aspartate, or glutamate.

6. The insulin derivative of claim 1, wherein:
the insulin B chain comprises the sequence set forth in SEQ ID NO:32; and the amino acid at position B29 is lysine, wherein the lysine is conjugated to a substituted or unsubstituted alkyl group or acyl group.

7. The insulin derivative of claim 6, wherein the lysine is conjugated to hexadecanedioic acid via a γ-L-glutamyl linker.

8. The insulin derivative of claim 1, wherein the cyclic amino acid is (2S, 4S)-4-hydroxy-L-proline.

9. The insulin derivative of claim 2, wherein the cyclic amino acid is (2S, 4S)-4-fluoro-L-proline.

10. The insulin derivative of claim 2, wherein the cyclic amino acid is (2S)-piperidine-2-carboxylic acid.

11. The insulin derivative of claim 2, wherein the cyclic amino acid is (2S)-4,4-difluoro-L-proline.

12. The insulin derivative of claim 2, wherein the cyclic amino acid is (4R)-1,3-thiazolidine-4-carboxylic acid.

13. A pharmaceutical composition, comprising the insulin derivative of claim 1.

14. The pharmaceutical composition of claim 8, wherein the composition is formulated for subcutaneous injection.

15. The pharmaceutical composition of claim 8, further comprising a second insulin derivative, wherein the second insulin derivative does not comprise the cyclic amino acid.

16. The pharmaceutical composition of claim 10, wherein the second insulin derivative is insulin comprising L-proline at the insulin B chain 28 position and lysine at the insulin B chain 29 position.

17. A method of making the insulin derivative of claim 1, comprising incubating cells comprising an insulin gene in a medium comprising the cyclic amino acid.

18. A method of making the insulin derivative of claim 1, comprising synthesizing the insulin B chain.

19. A method of making the insulin derivative of claim 1, comprising coupling a molecule comprising the cyclic amino acid to a peptide comprising either the insulin A chian, the insulin B chain, or both.

20. A method of treating hyperglycemia, type 2 diabetes, impaired glucose tolerance, type 1 diabetes, obesity, metabolic syndrome X, or dyslipidemia in a subject, comprising administering to the subject the pharmaceutical composition derivative of claim 13.

* * * * *

SEQUENCE LISTING

```
<160> NUMBER OF SEQ ID NOS: 33

<210> SEQ ID NO 1
<211> LENGTH: 21
<212> TYPE: PRT
<213> ORGANISM: Homo sapiens

<400> SEQUENCE: 1

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 2
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (28)..(29)
<223> OTHER INFORMATION: Any amino acid

<400> SEQUENCE: 2

Phe Val Asn Gln His Leu Cys Gly Ser His Leu Val Glu Ala Leu Tyr
1               5                   10                  15
```

Leu Val Cys Gly Glu Arg Gly Phe Phe Tyr Thr Xaa Xaa Thr
            20                  25                  30

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(11)
<223> OTHER INFORMATION: Any amino acid wherein at least one residue at
      these positions is a cyclic amino acid other than L-proline
<220> FEATURE:
<223> OTHER INFORMATION: See specification as filed for detailed
      description of substitutions and preferred embodiments

<400> SEQUENCE: 3

Ser Gly Glu Arg Gly Phe Phe Tyr Thr Xaa Xaa Thr
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(10)
<223> OTHER INFORMATION: Any amino acid wherein at least one residue at
      these positions is a cyclic amino acid other than L-proline
<220> FEATURE:
<223> OTHER INFORMATION: See specification as filed for detailed
      description of substitutions and preferred embodiments

<400> SEQUENCE: 4

Gly Glu Arg Gly Phe Phe Tyr Thr Xaa Xaa Thr
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(9)
<223> OTHER INFORMATION: Any amino acid wherein at least one residue at
      these positions is a cyclic amino acid other than L-proline
<220> FEATURE:
<223> OTHER INFORMATION: See specification as filed for detailed
      description of substitutions and preferred embodiments

<400> SEQUENCE: 5

Glu Arg Gly Phe Phe Tyr Thr Xaa Xaa Thr
1               5                   10

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES

```
<222> LOCATION: (7)..(8)
<223> OTHER INFORMATION: Any amino acid wherein at least one residue at
      these positions is a cyclic amino acid other than L-proline
<220> FEATURE:
<223> OTHER INFORMATION: See specification as filed for detailed
      description of substitutions and preferred embodiments

<400> SEQUENCE: 6

Arg Gly Phe Phe Tyr Thr Xaa Xaa Thr
1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(7)
<223> OTHER INFORMATION: Any amino acid wherein at least one residue at
      these positions is a cyclic amino acid other than L-proline
<220> FEATURE:
<223> OTHER INFORMATION: See specification as filed for detailed
      description of substitutions and preferred embodiments

<400> SEQUENCE: 7

Gly Phe Phe Tyr Thr Xaa Xaa Thr
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(6)
<223> OTHER INFORMATION: Any amino acid wherein at least one residue at
      these positions is a cyclic amino acid other than L-proline
<220> FEATURE:
<223> OTHER INFORMATION: See specification as filed for detailed
      description of substitutions and preferred embodiments

<400> SEQUENCE: 8

Phe Phe Tyr Thr Xaa Xaa Thr
1               5

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(5)
<223> OTHER INFORMATION: Any amino acid wherein at least one residue at
      these positions is a cyclic amino acid other than L-proline
<220> FEATURE:
<223> OTHER INFORMATION: See specification as filed for detailed
      description of substitutions and preferred embodiments

<400> SEQUENCE: 9

Phe Tyr Thr Xaa Xaa Thr
1               5
```

```
<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(4)
<223> OTHER INFORMATION: Any amino acid wherein at least one residue at
      these positions is a cyclic amino acid other than L-proline
<220> FEATURE:
<223> OTHER INFORMATION: See specification as filed for detailed
      description of substitutions and preferred embodiments

<400> SEQUENCE: 10

Tyr Thr Xaa Xaa Thr
1               5

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Any amino acid wherein at least one residue at
      these positions is a cyclic amino acid other than L-proline
<220> FEATURE:
<223> OTHER INFORMATION: See specification as filed for detailed
      description of substitutions and preferred embodiments

<400> SEQUENCE: 11

Thr Xaa Xaa Thr
1

<210> SEQ ID NO 12
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Any amino acid wherein at least one residue at
      these positions is a cyclic amino acid other than L-proline
<220> FEATURE:
<223> OTHER INFORMATION: See specification as filed for detailed
      description of substitutions and preferred embodiments

<400> SEQUENCE: 12

Xaa Xaa Thr
1

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(11)
<223> OTHER INFORMATION: Any amino acid wherein at least one residue at
      these positions is a cyclic amino acid other than L-proline
<220> FEATURE:
```

```
<223> OTHER INFORMATION: See specification as filed for detailed
      description of substitutions and preferred embodiments

<400> SEQUENCE: 13

Ser Gly Glu Arg Gly Phe Phe Tyr Thr Xaa Xaa
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(10)
<223> OTHER INFORMATION: Any amino acid wherein at least one residue at
      these positions is a cyclic amino acid other than L-proline
<220> FEATURE:
<223> OTHER INFORMATION: See specification as filed for detailed
      description of substitutions and preferred embodiments

<400> SEQUENCE: 14

Gly Glu Arg Gly Phe Phe Tyr Thr Xaa Xaa
1               5                   10

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(9)
<223> OTHER INFORMATION: Any amino acid wherein at least one residue at
      these positions is a cyclic amino acid other than L-proline
<220> FEATURE:
<223> OTHER INFORMATION: See specification as filed for detailed
      description of substitutions and preferred embodiments

<400> SEQUENCE: 15

Glu Arg Gly Phe Phe Tyr Thr Xaa Xaa
1               5

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(8)
<223> OTHER INFORMATION: Any amino acid wherein at least one residue at
      these positions is a cyclic amino acid other than L-proline
<220> FEATURE:
<223> OTHER INFORMATION: See specification as filed for detailed
      description of substitutions and preferred embodiments

<400> SEQUENCE: 16

Arg Gly Phe Phe Tyr Thr Xaa Xaa
1               5

<210> SEQ ID NO 17
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(7)
<223> OTHER INFORMATION: Any amino acid wherein at least one residue at
      these positions is a cyclic amino acid other than L-proline
<220> FEATURE:
<223> OTHER INFORMATION: See specification as filed for detailed
      description of substitutions and preferred embodiments

<400> SEQUENCE: 17

Gly Phe Phe Tyr Thr Xaa Xaa
1               5

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(6)
<223> OTHER INFORMATION: Any amino acid wherein at least one residue at
      these positions is a cyclic amino acid other than L-proline
<220> FEATURE:
<223> OTHER INFORMATION: See specification as filed for detailed
      description of substitutions and preferred embodiments

<400> SEQUENCE: 18

Phe Phe Tyr Thr Xaa Xaa
1               5

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(5)
<223> OTHER INFORMATION: Any amino acid wherein at least one residue at
      these positions is a cyclic amino acid other than L-proline
<220> FEATURE:
<223> OTHER INFORMATION: See specification as filed for detailed
      description of substitutions and preferred embodiments

<400> SEQUENCE: 19

Phe Tyr Thr Xaa Xaa
1               5

<210> SEQ ID NO 20
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(4)
<223> OTHER INFORMATION: Any amino acid wherein at least one residue at
      these positions is a cyclic amino acid other than L-proline
<220> FEATURE:
<223> OTHER INFORMATION: See specification as filed for detailed
      description of substitutions and preferred embodiments

<400> SEQUENCE: 20
```

Tyr Thr Xaa Xaa
1

<210> SEQ ID NO 21
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Any amino acid wherein at least one residue at
      these positions is a cyclic amino acid other than L-proline
<220> FEATURE:
<223> OTHER INFORMATION: See specification as filed for detailed
      description of substitutions and preferred embodiments

<400> SEQUENCE: 21

Thr Xaa Xaa
1

<210> SEQ ID NO 22
<211> LENGTH: 24
<212> TYPE: PRT
<213> ORGANISM: Unknown
<220> FEATURE:
<223> OTHER INFORMATION: Description of Unknown:
      signal peptide

<400> SEQUENCE: 22

Met Ala Leu Trp Met Arg Leu Leu Pro Leu Leu Ala Leu Leu Ala Leu
1               5                   10                  15

Trp Gly Pro Asp Pro Ala Ala Ala
            20

<210> SEQ ID NO 23
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (52)..(53)
<223> OTHER INFORMATION: Any amino acid wherein at least one residue at
      these positions is a cyclic amino acid other than L-proline
<220> FEATURE:
<223> OTHER INFORMATION: See specification as filed for detailed
      description of substitutions and preferred embodiments

<400> SEQUENCE: 23

Met Ala Leu Trp Met Arg Leu Leu Pro Leu Leu Ala Leu Leu Ala Leu
1               5                   10                  15

Trp Gly Pro Asp Pro Ala Ala Ala Phe Val Asn Gln His Leu Cys Gly
            20                  25                  30

Ser His Leu Val Glu Ala Leu Tyr Leu Val Cys Gly Glu Arg Gly Phe
        35                  40                  45

Phe Tyr Thr Xaa Xaa Thr Arg Arg Glu Ala Glu Asp Leu Gln Val Gly
    50                  55                  60

Gln Val Glu Leu Gly Gly Gly Pro Gly Ala Gly Ser Leu Gln Pro Leu
65                  70                  75                  80

Ala Leu Glu Gly Ser Leu Gln Lys Arg Gly Ile Val Glu Gln Cys Cys
                85                  90                  95

Thr Ser Ile Cys Ser Leu Tyr Gln Leu Glu Asn Tyr Cys Asn
            100                 105                 110

<210> SEQ ID NO 24
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Phe Val Asn Gln His Leu Cys Gly Ser His Leu Val Glu Ala Leu Tyr
1               5                   10                  15

Leu Val

<210> SEQ ID NO 25
<211> LENGTH: 12
<212> TYPE: PRT
<213> ORGANISM: Homo sapiens

<400> SEQUENCE: 25

Arg Gly Phe Phe Tyr Thr Pro Lys Thr Arg Arg Glu
1               5                   10

<210> SEQ ID NO 26
<211> LENGTH: 294
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
atgagaggat cgcatcacca tcaccatcac cgctttgtga accagcacct gtgcggtagc      60
cacctggtgg aagctctgta cctggtttgc ggtgagcgtg gtttcttcta cacgccaaag     120
acccgccgtg aagctgaaga tctgcaggtg ggccaggtag aactgggcgg tggtccgggt     180
gccggctctc tgcaaccgct ggcactggaa ggttccctgc aagcgcgtgg tatcgtagag     240
cagtgctgta cttctatctg ctccctgtac cagctggaga actactgtaa ttaa           294

<210> SEQ ID NO 27
<211> LENGTH: 97
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Met Arg Gly Ser His His His His His His Arg Phe Val Asn Gln His
1               5                   10                  15

Leu Cys Gly Ser His Leu Val Glu Ala Leu Tyr Leu Val Cys Gly Glu
            20                  25                  30

Arg Gly Phe Phe Tyr Thr Pro Lys Thr Arg Arg Glu Ala Glu Asp Leu
        35                  40                  45

Gln Val Gly Gln Val Glu Leu Gly Gly Gly Pro Gly Ala Gly Ser Leu
    50                  55                  60

Gln Pro Leu Ala Leu Glu Gly Ser Leu Gln Ala Arg Gly Ile Val Glu
65                  70                  75                  80

Gln Cys Cys Thr Ser Ile Cys Ser Leu Tyr Gln Leu Glu Asn Tyr Cys

<210> SEQ ID NO 28
<211> LENGTH: 294
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 28

```
atgagaggat cgcatcacca tcaccatcac cgctttgtga accagcacct gtgcggtagc      60
cacctggtgg aagctctgta cctggtttgc ggtgagcgtg gtttcttcta cacgaagccg     120
acccgccgtg aagctgaaga tctgcaggtg ggccaggtag aactgggcgg tggtccgggt     180
gccggctctc tgcaaccgct ggcactggaa ggttccctgc aagcgcgtgg tatcgtagag     240
cagtgctgta cttctatctg ctccctgtac cagctggaga actactgtaa ttaa            294
```

<210> SEQ ID NO 29
<211> LENGTH: 97
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 29

```
Met Arg Gly Ser His His His His His His Arg Phe Val Asn Gln His
1               5                   10                  15
Leu Cys Gly Ser His Leu Val Glu Ala Leu Tyr Leu Val Cys Gly Glu
            20                  25                  30
Arg Gly Phe Phe Tyr Thr Lys Pro Thr Arg Arg Glu Ala Glu Asp Leu
        35                  40                  45
Gln Val Gly Gln Val Glu Leu Gly Gly Gly Pro Gly Ala Gly Ser Leu
    50                  55                  60
Gln Pro Leu Ala Leu Glu Gly Ser Leu Gln Ala Arg Gly Ile Val Glu
65                  70                  75                  80
Gln Cys Cys Thr Ser Ile Cys Ser Leu Tyr Gln Leu Glu Asn Tyr Cys
                85                  90                  95
Asn
```

<210> SEQ ID NO 30
<211> LENGTH: 294
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 30

```
atgagaggat cgcatcacca tcaccatcac cgctttgtga accagcacct gtgcggtagc      60
cacctggtgg aagctctgta cctggtttgc ggtgagcgtg gtttcttcta cacgccaccg     120
acccgccgtg aagctgaaga tctgcaggtg ggccaggtag aactgggcgg tggtccgggt     180
gccggctctc tgcaaccgct ggcactggaa ggttccctgc aagcgcgtgg tatcgtagag     240
cagtgctgta cttctatctg ctccctgtac cagctggaga actactgtaa ttaa            294
```

<210> SEQ ID NO 31

```
<211> LENGTH: 97
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Met Arg Gly Ser His His His His His His Arg Phe Val Asn Gln His
1               5                   10                  15

Leu Cys Gly Ser His Leu Val Glu Ala Leu Tyr Leu Val Cys Gly Glu
                20                  25                  30

Arg Gly Phe Phe Tyr Thr Pro Pro Thr Arg Arg Glu Ala Glu Asp Leu
            35                  40                  45

Gln Val Gly Gln Val Glu Leu Gly Gly Gly Pro Gly Ala Gly Ser Leu
        50                  55                  60

Gln Pro Leu Ala Leu Glu Gly Ser Leu Gln Ala Arg Gly Ile Val Glu
65                  70                  75                  80

Gln Cys Cys Thr Ser Ile Cys Ser Leu Tyr Gln Leu Glu Asn Tyr Cys
                85                  90                  95

Asn

<210> SEQ ID NO 32
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (28)..(29)
<223> OTHER INFORMATION: Any amino acid

<400> SEQUENCE: 32

Phe Val Asn Gln His Leu Cys Gly Ser His Leu Val Glu Ala Leu Tyr
1               5                   10                  15

Leu Val Cys Gly Glu Arg Gly Phe Phe Tyr Thr Xaa Xaa
                20                  25

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 33

His His His His His His
1               5
```

UNITED STATES PATENT AND TRADEMARK OFFICE
CERTIFICATE OF CORRECTION

| | |
|---|---|
| PATENT NO. | : 10,640,546 B2 |
| APPLICATION NO. | : 14/735742 |
| DATED | : May 5, 2020 |
| INVENTOR(S) | : David A. Tirrell et al. |

It is certified that error appears in the above-identified patent and that said Letters Patent is hereby corrected as shown below:

In the Claims

In Claim 14, appearing at Column 45, Line 19, please replace:
"claim 8,"
With:
--claim 13,--.

In Claim 15, appearing at Column 46, Line 1, please replace:
"claim 8,"
With:
--claim 13,--.

In Claim 16, appearing at Column 46, Line 4, please replace:
"claim 10,"
With:
--claim 15,--.

Signed and Sealed this
Twenty-third Day of May, 2023

*Katherine Kelly Vidal*

Katherine Kelly Vidal
*Director of the United States Patent and Trademark Office*